US006692751B1

(12) United States Patent
Zebedee et al.

(10) Patent No.: US 6,692,751 B1
(45) Date of Patent: Feb. 17, 2004

(54) METHODS AND SYSTEMS FOR PRODUCING RECOMBINANT VIRAL ANTIGENS

(75) Inventors: Suzanne Zebedee, Carlsbad, CA (US); Genevieve Inchauspe, Lyons (FR); Marc S. Nasoff, San Diego, CA (US); Alfred S. Prince, Pound Ridge, NY (US); Torsten B. Helting, P.O. Box 880963, San Francisco, CA (US) 94188; Michael F. Nunn, Washington, DC (US)

(73) Assignees: New York Blood Center, New York, NY (US); by said Genevieve Inchauspe and Alfred Prince; Torsten B. Helting, San Francisco, CA (US); by said Marc Nasoff and Michael Nunn ( * ) Notice: Subject to any disclaimer, the term of this patent is extended or adjusted under 35 U.S.C. 154(b) by 0 days.

(21) Appl. No.: 08/931,855

(22) Filed: Sep. 16, 1997

Related U.S. Application Data

(63) Continuation-in-part of application No. 08/563,733, filed on Nov. 28, 1995, now abandoned, which is a division of application No. 08/049,531, filed on Apr. 20, 1993, now Pat. No. 5,470,720, which is a division of application No. 07/344,237, filed on Apr. 26, 1989, now Pat. No. 5,204,259, which is a continuation-in-part of application No. 07/258,016, filed on Oct. 14, 1988, now abandoned, and a continuation-in-part of application No. 07/206,499, filed on Jun. 13, 1988, now abandoned, and a continuation-in-part of application No. 07/191,229, filed on May 6, 1988, now abandoned, application No. 08/931,855, which is a continuation-in-part of application No. 08/272,271, filed on Jul. 8, 1994, now abandoned, which is a continuation of application No. 07/616,369, filed on Nov. 21, 1990, now abandoned, which is a continuation-in-part of application No. 07/573,643, filed on Aug. 27, 1990, now abandoned.

(51) Int. Cl.$^7$ .............................................. A61K 39/29
(52) U.S. Cl. ................ 424/228.1; 435/69.1; 435/320.1; 536/24.1
(58) Field of Search ............................ 435/5, 2.1, 69.1, 435/69.7, 69.3, 320.1, 189.1; 424/192.1, 218.1

Primary Examiner—Laurie Scheiner
Assistant Examiner—J. S. Parkin
(74) Attorney, Agent, or Firm—Joseph E. Mueth

(57) ABSTRACT

The present invention relates to recombinant expression vectors which express segments of deoxyribonucleic acid that encode recombinant HIV and HCV antigens. These recombinant expression vectors are transformed into host cells and used in a method to express large quantities of these antigens. The invention also provides compositions containing certain of the isolated antigens., diagnostic systems containing these antigens and methods of assaying body fluids to detect the presence of antibodies against the antigens of the invention.

14 Claims, 9 Drawing Sheets

FROM LEFT TO RIGHT: p24-gp 41 of USP 5,470,720
p24-gp41 (Subtype O ANT)
p24-gp41 (Subtype O MVP5180)
p24-gp41 (Subtype x84328)
p24-gp 41 of USP 5,470,720
p24 of USP 5,470,720

FROM LEFT TO RIGHT: 5 sets of three different concentrations of NANB Hepatitis Capsid protein.
Right lane, Molecular weight reference proteins.

FROM LEFT TO RIGHT: Three stages of purification of NANB Hepatitis NS 3 794 recombinant Protein
RIGHT LANE: Molecular weight reference Protein.

METHODS AND SYSTEMS FOR PRODUCING RECOMBINANT VIRAL ANTIGENS

This is a continuation-in-part application of Ser. No. 08/563,733, filed Nov. 28, 1995, now abandoned which is a division of Ser. No. 08/049,531, filed Apr. 20, 1993, U.S. Pat. No. 5,470,720, which is a division of Ser. No. 07/344, 237, filed Apr. 26, 1989, U.S. Pat. No. 5,204,259, which is a continuation-in-part of Ser. No. 07/191,229, filed May 6, 1988, abandoned, Ser. No. 07/206,499, filed Jun. 13, 1988, abandoned and Ser. No. 07/258,016, filed Oct. 14, 1988, abandoned; and of Ser. No. 08/272,271, filed Jul. 8, 1994, now abandoned which is a continuation of Ser. No. 07/616, 369, filed Nov. 21, 1990, abandoned, which is a continuation-in-part of Ser. No. 07/573,643, filed Aug. 27, 1990, abandoned; the disclosures of which are incorporated herein by reference.

FIELD OF THE INVENTION

The present invention relates to recombinant expression vectors which have segments of deoxyribonucleic acid (DNA) that encode recombinant HIV and HCV antigens operatively linked to the sequence AGGAGGGTTTTCAT (nucleotides 1 to 15 of SEQ ID NO:1) to control expression of the antigens. These recombinant expression vectors are transformed into host cells and used in a method to express large quantities of these antigens. The invention also provides compositions containing certain of the isolated antigens, diagnostic systems containing these antigens and methods of assaying body fluids to. detect the presence of antibodies against the antigens of the invention.

BACKGROUND OF THE INVENTION

The development of immunoassays for the detection of antibodies has been limited by difficulties in producing sufficient quantities of specific antigens that are essentially free of immunoreactive contaminants. The presence of contaminants that react with antibodies present in patient samples results in lower assay specificity and sensitivity and an increase in false positive results. The production of large amounts of antigen enables easier purification of antigen having a higher degree of purity and thus less immunoreactive contaminants.

The present invention overcomes the difficulties by providing a simple and highly efficient expression system that allows for the Production of large quantities of antigens. The invention relies on the efficient expression resulting from the inclusion of the nucleotide sequence AGGAGGGTTTTCAT (which corresponds to nucleotides 1–15 of SEQ ID NO.:1) directly upstream from the ATG codon which marks the start of translation.

The invention is particularly useful for the expression of viral antigens of Human Immunodeficiency Virus (HIV) and Hepatitis C Virus (HCV).

HIV is the causative agent of Acquired Immunodeficiency Syndrome (AIDS). The nucleic acid sequence of the HIV proviral genome has been deduced and the location of various protein coding regions within the viral genome has been determined. Of particular interest to the present invention are the portions of the HIV genome known in the art as the gag and env regions. The gag region encodes a precursor protein that is cleaved and processed into three mature proteins, p17, p24 and p15. The HIV p24 protein has an apparent relative molecular weight of about 24,000 daltons and is known in the art as the HIV core antigen because it forms the viral capsid. Also of interest is the env region which encodes the envelope glycoproteins gp120 and gp41, which are required for viral entry into the cell. The first step in infection is the formation of a complex of gp120, gp41 and the cellular CD4 protein, binding the virus particle to the cell. The formation of this complex appears to alter the confirmation of gp41, allowing its interaction with a second cellular protein "fusin", an interaction required for HIV entry into the cell.

The p24 antigen of HIV is of particular interest because studies have indicated that the first evidence of anti-HIV antibody formation (sero-conversion) in infected individuals is the appearance of antibodies induced by the p24 antigen, i.e., anti-p24 antibodies. In addition, recent studies have reported that p24 protein can be detected in blood samples even before the detection of anti p24 antibodies. Detecting the presence of either the p24 protein or anti-p24 antibodies therefore appears to be the best approach to detecting HIV infection at the earliest point in time. Furthermore, the p24 antigen reappears in the blood of infected individuals concomitant with the decline of anti-p24 antibody in patients showing the deterioration in their clinical condition that accompanies transition into full-blown AIDS. Thus, the p24 antigen can serve as an effective prognostic marker in patients undergoing therapy.

Most cases of Non-A, non-B hepatitis (NANBH) are caused by the transmissible virus now designated as hepatitis C virus (HCV). Isolates of HCV nucleic acids have been obtained and completely characterized at the sequence level. The HCV genome is comprised of a plus strand RNA molecule that codes for a single polyprotein which is cleaved to produce functionally distinct structural and non-structural HCV proteins. Structural proteins include the capsid and envelope proteins which form the viral particle. Nonstructural proteins, such as helicase and RNA-directed RNA polymerase are required for viral function.

Some HCV gene products, or portions thereof have been expressed as fusion products. The HCV antigen C-100-3, derived from portions of the nonstructural genes designated NS3 and NS4, has been expressed as a fusion protein and used to detect anti-C-100-3 antibodies in patients with various forms of NANB hepatitis. See, for example, Kuo et al, *Science*, 244:362–364 (1989) and International Application No. PCT/US88/04125. A diagnostic assay based on C-100-3 antigen is commercially available from Ortho Diagnostics, Inc. (Raritan, N.J.). However, the C-100-3 antigen-based immunoassay has been reported to preferentially detect antibodies in sera from chronically infected patients. C-100-3 seroconversion generally occurs from four to six months after the onset of hepatitis, and in some cases C-100-3 fails to detect any antibody where an NANBV infection is present. Alter et al, *New Eng. J. Med.*, 321:1538–39 (1989); Alter et al, *New Eng. J. Med.*, 321:1494–1500 (1989); and Weiner et al, *Lancet*, 335:1–3 (1990). McFarlane et al, *Lancet*, 335:754–757 (1990), described false positive results when the C-100-3-based immunoassay was used to measure antibodies in patients with autoimmune chronic active hepatitis. In addition, Grey et al., *Lancet*, 335:609–610 (1990), describe false positive results using C-100-3-based immunoassay on sera from patients with liver disease caused-by a variety of conditions other than HCV. Houghton et al., U.S. Pat. No. 5,350,671, have disclosed a series of fusion proteins which include amino acids from parts of various structural and nonstructural HCV gene products fused to superoxide dismutase (SOD), many of which have no immunogenic activity when tested against HCV positive antisera.

The present invention provides compositions of recombinantly produced HIV and HCV antigens, free of bacterial and other viral components, thus enabling the detection of HIV and HCV antibodies with improved accuracy and sensitivity. The present invention also enables high yield expression of these antigens alone or as fusion proteins.

SUMMARY OF THE INVENTION

The present invention is directed to recombinant expression vectors which comprise a first nucleic acid having the sequence AGGAGGGTTTTTCAT (which corresponds to nucleotides 1–15 of SEQ ID NO.:1) operatively linked to a second nucleic acid having a sequence encoding an HIV or HCV antigen.

The preferred vectors of the inventions are pGEX7 derivatives. The pGEX7 vector contains the first nucelic acid sequence (AGGAGGGTTTTTCAT). Thus, the second nucleic acid encoding the HIV antigen or HCV antigen is operatively linked to pGEX7-derived first nucelic acid.

In addition to the recombinant expression vectors, the present invention includes host cells comprising these vectors, the recombinant HIV and HCV antigens produced by treating the host cells of the invention for a time and under conditions to cause expression of the antigen, the HIV and HCV antigens produced by this method and compositions comprising a recombinantly-produced HIV or HCV antigen of the invention. The compositions can be essentially free of procaryotic antigens or other viral-related proteins of the respective antigens.

The HIV antigen of the invention comprises three domans which are optionally joined by 1 to 5 linker amino acids. The first domain has a nucleotide sequence which encodes amino acids 1–225 of an HIV p24 antigen, the second domain has a nucleotide sequence which encodes an HIV gp41 antigen (or antigenic fragment thereof), and the third domain has a nucleotide sequence which encodes amino acids 224–232 of an HIV p24 antigen. In preferred embodiments the HIV antigen is encoded by amino acids 1–258 of SEQ ID NO:2, 4 or 6. These preferred HIV antigens are expressed from the vectors pGEXp24gp41-ANT, pGEXp24gp41-MVP and pGEXp24gp41-X84328, respectively.

The HCV antigens of the invention are the HCV capsid antigen, the HCV non-structural 794 antigen and the HCV CAP-B antigen. In preferred embodiments, the HCV capsid antigen is encoded by amino acids 1–120 from an HCV strain, and more preferably are encoded by amino acids 1–120 of SEQ ID NO:8, 10, 12 or 14. The preferred HCV capsid antigens are expressed from the vectors pGEX-C120H-V68, pGEX-C120H, pGEX-C120H-IS02 and pGEX-C120H-ISO3, respectively. In preferred embodiments the HCV non-structural 794 antigen is encoded by the amino acids of SEQ ID NO: 16 or the corresponding sequence from another HCV strain. The antigen of SEQ ID NO: 16 is preferably expressed from pGEX-NS3-794. The CAP-B antigen is encoded by the amino acids of SEQ ID NO: 18 or the corresponding sequence from another HCV strain. The antigen of SEQ ID NO: 18 is preferably expressed from pGEX-CAP-B.

Another aspect of the invention is directed to a diagnostic kit comprising an amount of a HIV antigen or HCV antigen composition of the invention sufficient to perform at least one assay.

Yet another aspect of the invention provides a method of assaying a body fluid sample for the presence of antibodies against an HIV or HCV antigen which comprises:
 a) forming an immunoreaction admixture by admixing the body fluid sample with a composition of the invention;
 b) maintaining the immunoreaction admixture for a time period sufficient for antibodies present against the desired antigen to immunoreact with the antigen and to form an immunoreaction product; and
 c) detecting the presence of any immunoreaction product formed and thereby the presence of the desired antibodies.

The method of claim 15, wherein said detecting in step (c) can further comprise the steps of:
 (i) admixing the immunoreaction product with a labeled specific binding agent to form a labeling admixture, wherein the labeled specific binding agent comprises a specific binding agent and a label;
 (ii) maintaining the labeling admixture for a time period sufficient for any immunoreaction product present to bind with the labeled specific binding agent to form a labeled product; and
 (iii) detecting the presence of any labeled product formed, and thereby the presence of the immunoreaction product.

In preferred embodiments, the specific binding agent can be Protein A, anti-human IgG or anti-human IgM and the label can be biotin, an enzyme, a lanthanide chelate or a radioactive isotope.

Further still, another embodiment of the invention is directed to a composition comprising the HCV capsid antigen of the invention and the HCV nonstructural 794 antigen of the invention which is essentially free of procaryotic antigens and other HCV-related proteins. These compositions can be provided as diagnostic kits and used in the methods of assaying a body fluid to detect antibodies against an HCV capsid antigen or an HCV nonstructural antigen as described above.

DETAILED DESCRIPTION OF THE INVENTION

A. Definitions

Figure 1:
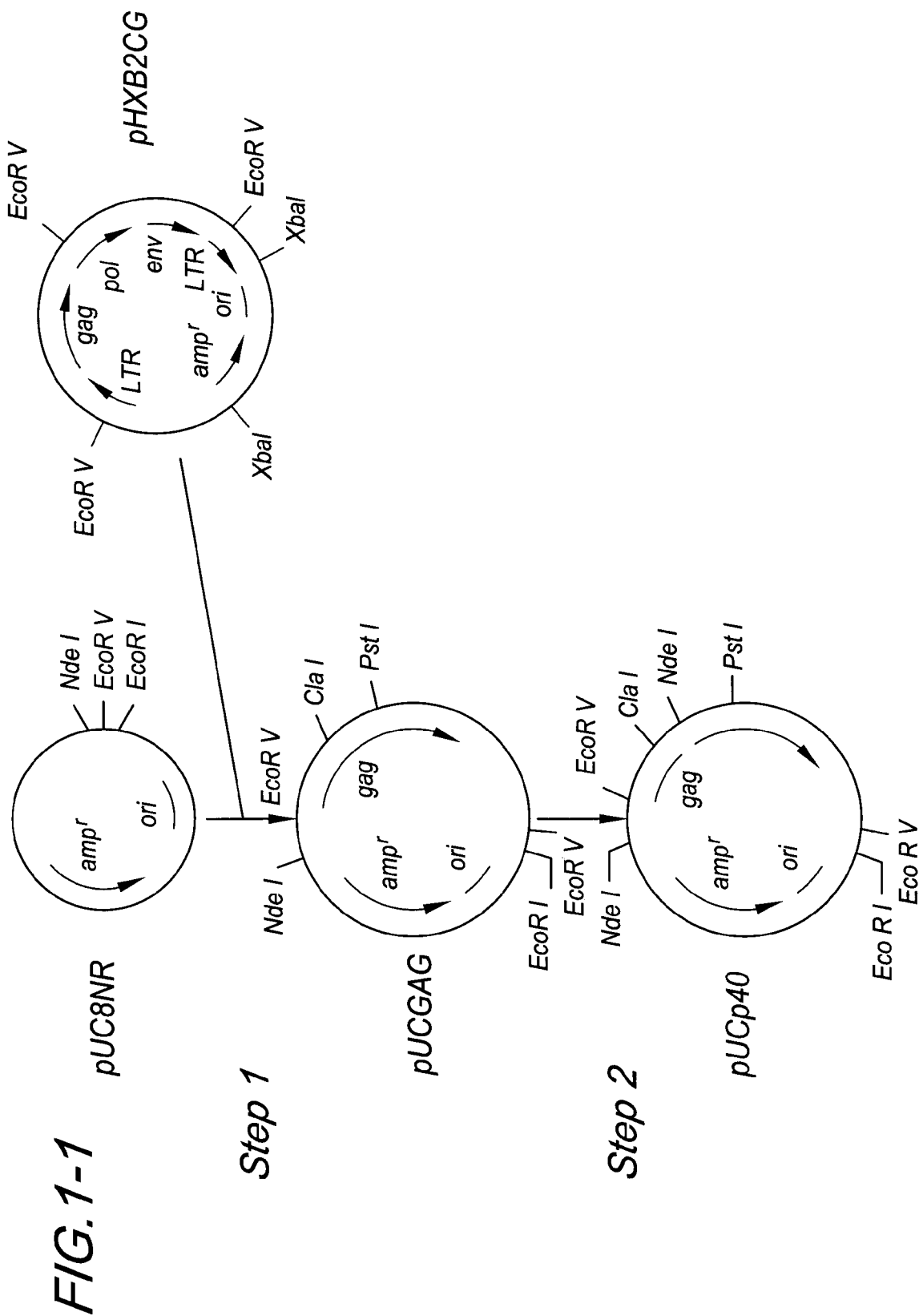
FIG. 1 illustrates the plasmid pGEXp24 for expressing recombinant HIV p24 protein in *E. coli*. The recombinant DNAs manipulated and produced by the construction process are indicated in the figure by the circles. The construction proceeds by a series of steps as indicated by the arrows connecting the circles in the figure and as described in detail in Example 1. Landmark and utilized restriction enzyme recognition sites are indicated on the circles by labeled lines intersecting the circles. The relative location of individual genes and their direction of transcription are indicated by the labeled arrows inside the circles.

Amino acid: All amino acid residues identified herein are in the natural L-configuration. All abbreviations for amino acid residues are in keeping with the standard polypeptide nomenclature, *J. Biol. Chem.* 243: 3557–3559 (1969). It should be noted that all amino acid residue sequences, typically referred to herein as "residue sequences" are represented herein by formulae whose left to right orientation is in the conventional direction of amino terminus to carboxy-terminus.

Nucleotide: a monomeric unit of DNA or RNA consisting of a sugar moiety (pentose) a phosphate and a nitrogenous heterocyclic base. The base is linked to the sugar moiety via the glycoside carbon (1' carbon of the pentose) and that combination of base and sugar is a nucleoside. When the nucleoside contains a phosphate group bonded to the 3' or 5' position of the pentose, it is referred to as a nucleotide. A sequence of operatively linked nucleotides is typically referred to herein as a "base sequence" and it is represented herein by the formula whose left to right orientation is in the conventional direction of 5' terminus to 3' terminus.

Base pair (bp): a partnership of adenine (A) with thymine (T), or of cytosine (C) with guanine (G) in a double stranded DNA molecule.

Antigen: a protein or polypeptide portion thereof which is immunologically identifiable. By immunologically identifiable is meant that the protein or polypeptide reacts specifically with naturally occurring or synthetically derived antibodies to form a complex of bound antibody and antigen.

Operatively linked: the juxtaposition of sequence elements, regulatory elements, control sequences and the like with coding sequences for a gene product, wherein the elements so described are joined to one another in a relationship permitting them to function in their intended manner, e.g. to control expression. A control sequence operatively linked to a coding sequence is spatially joined in such a way that expression of the coding sequence is achieved under conditions compatible with the control sequences. A second coding sequence may be operatively linked to an expressed first coding sequence such that the regulatory elements and control sequences of the first coding region govern expression of the second coding sequence as well. In the present invention, operatively linked coding sequences are juxtaposed such that a single expression product is produced which comprises regions from each of the coding sequences.

HIV antigen: As referred to in the current invention, HIV antigen means an HIV p24gp41 hybrid protein which comprises an amino acid sequence from gp41 flanked on its amino terminus by amino acids 1–225 of a HIV p24 protein and on its carboxy terminus by amino acids 224–232 of a HIV p24 protein. In some instances, the sequences of each protein domain can be joined by 1–5 linker amino acids. Exemplary antigens are expressed by plasmids pGEXp24gp41-ANT, pGEXp24gp41-MVP or pGEXp24gp41-X84328 of the present invention.

HCV antigen: As referred to herein, HCV antigen means an HCV CAP-B antigen, an HCV 1–120 capsid antigen or an HCV nonstructural 794 antigen. A nonstructural antigen, in the context of HCV means an antigen not derived from capsid or envelope proteins. An HCV CAP-B antigen consists of amino acid residues 1–220 of glutathione-S-transferase, an intermediate polypeptide portion corresponding to residues 221–226 and defining a cleavage site for the protease Thrombin, a polypeptide portion corresponding to residues 227–246 and defining residues 21–40 of an HCV capsid antigen (exemplified by GenBank accession no. M67463) and with or without a carboxy-terminal tail corresponding to residues 247–252. An HCV 1–120 capsid antigen consists of amino acid residues 1 to 120 of an HCV polyprotein. Herein exemplified are an HCV 1–120 capsid antigen derived from HCV strain Hutch and three homologues with various amino acid substitutions. An HCV nonstructural 794 antigen consists of amino acid residues 1–10 having six histidine residues at positions 4 to 9, a nonstructural NS3 antigen of HCV strain Hutch from residue 11 to residue 115 and a six residue tail. The nonstructural NS3 antigen disclose herein corresponds to amino acid residues 1352 to 1456 of the amino acid sequence disclosed in GenBank accession no. 130461. Examples of HCV antigens are encoded by plasmids pGEX-C120H-V68, pGEX-C120H, pGEX-C120H-ISO2, pGEX-C 120H-ISO3, pGEX-NS3-794 and pGEX-CAP-B1 of the current invention.

B. Recombinant DNA Molecules

In living organisms, the amino acid residue sequence of a protein or polypeptide is directly related via the genetic code to the DNA sequence of the structural gene that codes for the protein. Thus, a structural gene can be defined in terms of the amino acid residue sequence, i.e., protein or polypeptide for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Occasionally, a methylated variant of a purine or pyrimidine may be incorporated into a given nucleotide sequence. However, such methylations do not affect the coding relationship in any way.

DNA sequences have other functions as well. Expression of a gene product, i.e. transcription of DNA sequences into ribonucleic acid (RNA) sequences and translation of messenger RNA (mRNA) into sequences of amino acids, depends on DNA nucleotide sequences in addition to those which actually encode the amino acid sequence of interest.

A DNA segment of the present invention comprises a first nucleotide base sequence that defines a ribosome binding site and has a sequence by the formula:

AGGAGGGTTTTTCAT (which corresponds to lnucleotides 1–15 of SEQ ID NO.:1).

The first sequence is joined at its 3' terminus to the 5' terminus of a second nucleotide base sequence that defines the structural gene product of interest. Structural gene products may include natural proteins, polypeptides, fusion proteins and proteins to which additional sequences of amino acids with specific functions have been added. Preferred DNA segments are illustrated in SEQ ID NO: 1, 3, 5, 7, 9, 11, 13, 15 and 17 and further include the base sequence TAA or similar sequences representing one or several stop signals, operatively linked to the 3' terminus of the structural gene. The base sequences are shown conventionally from left to right and in the direction of 5' terminus to 3' terminus of the coding sequence using the single letter nucleotide base code (A=Adenine, T=Thymine, C=Cytosine and G=Guanine). Nucleotide bases 1–4 represent the Shine Delgarno sequence (Shine et al. *Proc. Natl. Acad. Sci. USA Natl. Acad. Sci. USA Natl Acad. Sci USA* 71:1342 (1974)). Bases 1–15 of the above listed sequences define the 15 bases AGGAGGGTTTTTCAT immediately preceding the nucleotide sequence encoding the antigen of interest, said 15 bases positioned immediately upstream of the polylinker cloning site of the ATCC deposited vector pGEX7 referred to herein. The amino acid sequences of the products expressed from the preferred DNA segments are given by SEQ ID NO: 2, 4, 6, 8, 10, 12, 14, 16 and 18.

In one embodiment of this invention, a DNA segment has the nucleotide sequence AGGAGGGTTTTTCAT joined to a nucleotide base sequence that defines an HIV antigen such as an HIV p24-gp41 hybrid protein. The phrase "HIV p24-gp41 hybrid protein" refers to a protein having an amino-terminal HIV p24 polypeptide portion joined by a peptide bond at its carboxy-terminus to an HMV gp41 polypeptide portion followed by another HMV p24 polypeptide portion. In the expressed protein, the first HIV p24 polypeptide portion has an amino acid residue sequence corresponding to residue 2 to residue 225 from one of the sequences shown in SEQ ID NO:2, 4 or 6. The second HIV p24 polypeptide portion has an amino acid sequence corresponding to residues 224 to 232 of an HMV p24 protein, which correspond to residues 250 to 258 of SEQ ID NOS: 2, 4 and 6 for the expressed HIV p24-gp41 hybrid protein.

The HIV gp41 polypeptide portion has an amino acid residue sequence corresponding to a polypeptide capable of immunoreacting with anti-HIV gp41 antibodies, i.e., a polypeptide displaying HIV gp41 antigenicity (an HMV gp41-antigenic polypeptide). Polypeptides displaying HMV gp41 antigenicity are well known in the art. See, for example, the U.S. Pat. No. 4,629,783 to Cosand, U.S. Pat. No. 4,735,896 to Wang et al., and Kennedy et al., Science, 231:1556–1559 (1986).

In preferred embodiments, the HIV gp41 polypeptide portion of the HIV p24-gp41 fusion protein of this invention contains at least 10 amino acid residues, but no more than about 35 amino acid residues, and preferably has a length of about 15 to about 30 residues. A preferred HIV gp41 polypeptide portion of a HIV p24-gp41 hybrid protein has an amino acid residue sequence represented by residue 227 to residue 249 shown in SEQ ID NO:2, by residue 227 to residue 249 shown in SEQ ID NO:4 or by residue 227 to residue 249 shown in SEQ ID NO:6.

In preferred embodiments, that portion of a HIV p24-gp41 hybrid protein encoding DNA segment of this invention that codes for the first HIV p24 polypeptide portion has a nucleotide base sequence corresponding to a sequence that codes for an amino acid residue sequence as shown in SEQ ID NOS:2, 4 and 6 from residue 1 to about residue 225, and more preferably has a nucleotide base sequence corresponding to a base sequence as shown in SEQ ID NOS:1, 3 and 5 from base 16 to base 690.

In preferred embodiments, that portion of a HIV p24-gp41 hybrid protein encoding DNA segment of this invention that codes for the HIV gp4l polypeptide portion has a nucleotide base sequence corresponding to a sequence that codes for an amino acid residue sequence as shown in SEQ ID NO:2 from residue 227 to residue 249, in SEQ ID NO:4 from residue 227 to residue 249, or in SEQ ID NO:6 from residue 227 to residue 249. More preferably that portion of the DNA segment coding for the HIV gp41 polypeptide portion has a nucleotide base segment corresponding in base sequence to the sequence shown in SEQ ID NO:1 from base 694 to base 762, in SEQ ID NO:3 from base 694 to base 762, or in SEQ ID NO:5 from base 694 to base 762.

In preferred embodiments, that portion of a HIV p24-gp41 hybrid protein encoding DNA segment of this invention that codes for the second HIV p24 polypeptide portion has a nucelotide base sequence corresponding to a sequence that codes for an amino acid sequence as shown in SEQ ID NOS: 2, 4 and 6 from residue 250 to 258, and more preferably has a nucleotide base sequence corresponding to a base sequence as shown in SEQ ID NOS 1, 3 and 5 from base 763 to base 789.

Several HIV Type I, subtype O conserved sequences are well known. (see, e.g., Cohen et al. *Lancet*, 345 p. 856, 1995, or GenBank Accession # X84328). In a particularly preferred embodiment, recombinant HIV p24-gp[41] hybrid protein is identified by SEQ ID NO:2 and contains an amino terminal p24 polypeptide portion (residues 2–225) followed by a Lys residue as linker amino acid to an intermediate, type 0 (strain ANT) specific HIV envelope portion (residues 227–249), and a carboxy terminal HIV p24 polypeptide portion (residues 250–258).

A second particularly preferred recombinant HIV p24-gp41 hybrid protein is identified by SEQ ID NO:4, wherein residues 227–249 correspond to a type 0 specific HIV envelope portion of strain MVP. A third particularly preferred recombinant HIV p24-gp41 hybrid protein is identified by SEQ ID NO:6. In this hybrid protein, the intermediate linker amino acid residue at position 226 is Gin and residues 227–249 correspond to a type 0 specific HIV envelope portion of strain GenBank X84328.

Most preferably, a HIV p24-gp41 hybrid protein encoding DNA segment of this invention has a nucleotide base sequence corresponding to the sequence shown in SEQ ID NO:1 from base 1 to base 795, in SEQ ID NO:3 from base 1 to base 795, or in SEQ ID NO:5 from base 1 to base 795.

In another embodiment of this invention, the nucleotide sequence AGGAGGGTTTTTCAT is joined to a nucleotide base sequence that defines the HCV antigen which is an HCV CAP-B fusion protein. The phrase "CAP-B" refers to a recombinant protein having a first glutathione-S-transferase (GST) polypeptide portion joined by a peptide bond at its carboxy terminus to a second intermediate polypeptide portion defining a cleavage site for Thrombin, said second portion joined by a peptide bond at its carboxy terminus to a third polypeptide portion defining an HCV capsid antigen consisting of amino acids 21–40 of an HCV capsid protein and a six residue tail.

The GST portion of a recombinant CAP-B antigen has an amino acid residue sequence corresponding to a sequence as shown in SEQ ID NO:18 from residue 2 to about residue 220, the amino terminal methionine being cleaved after translation. An intermediate polypeptide portion defining a thrombin cleavage site has the amino acid sequence shown in SEQ ID NO:18 from residue 221 to residue 226.

SEQ ID NO:18 illustrates the amino acid sequence of a particularly preferred recombinant CAP-B fusion protein wherein amino acids 1–220 are from GST, residues 221–226 are a cleavage site for protease Thrombin, residues 227 to 246 are from the HCV capsid antigen with the amino acid sequence of residues 21–40 from GenBank accession no. M67463 (strain Hutch) and residues 247 to 252 are a carboxy terminal tail.

In preferred embodiments, that portion of a CAP-B protein encoding DNA segment of this invention that codes for the GST portion has a nucleotide base sequence corresponding to a sequence that codes for an amino acid residue sequence as shown in SEQ ID NO:18 from about residue 1 to about residue 220 and more preferably has a nucleotide base sequence corresponding to a base sequence as shown in SEQ ID NO:17 from base 16 to base 675.

In preferred embodiments, that portion of a CAP-B protein encoding DNA segment of this invention that codes for the intermediate polypeptide portion defining a thrombin cleavage site has a nucleotide base sequence corresponding to a sequence that codes for an amino acid residue sequence as shown in SEQ ID NO:18 from residue 221 to residue 226 and more preferably has a nucleotide base sequence corresponding to a base sequence as shown in SEQ ID NO:17 from base 676 to base 693.

In preferred embodiments, that portion of a CAP-B protein encoding DNA segment of this invention that codes for the HCV 21-40 capsid portion has a nucleotide base sequence corresponding to a sequence that codes for an amino acid residue sequence as shown in SEQ ID NO:18 from residue 227 to residue 246 and more preferably has a nucleotide base sequence corresponding to a base sequence shown in SEQ ID NO:17 from base 694 to base 753.

In a particularly preferred embodiment, the CAP-B protein encoding DNA segment codes for an amino acid residue sequence as shown in SEQ ID NO:18 from residue 1 to residue 252. Most preferably, a CAP-B protein encoding DNA segment of this invention has a nucleotide base sequence corresponding to the sequence disclosed by SEQ ID NO:17 from base 1 to base 774, and consists of a ribosome binding site, coding sequence and a stop codon for expression of the HCV strain Hutch CAP-B antigen.

This invention is further embodied by a DNA segment with the nucleotide sequence AGGAGGGTTTTTCAT joined to a nucleotide base sequence that defines the HCV antigen which is an HCV 1–120 capsid antigen. The phrase "capsid antigen" refers to a recombinant protein consisting of amino acids 1–120 of HCV. Preferably, the capsid protein is immunologically related to the Hutch strain of HCV (amino acid sequence 1–120 of GenBank accession no. M67463).

A preferred recombinant HCV capsid antigen is illustrated by SEQ ID NO:8 which represents the structural polypeptide of HCV strain Hutch (amino acid residues 1–120) exhibiting a substitution from Alanine to Valine at amino acid residue 68. Another preferred recombinant HCV capsid antigen is illustrated by SEQ ID NO: 10 which represents the structural polypeptide of HCV strain Hutch. A third recombinant HCV capsid antigen is illustrated by SEQ ID NO:12 which represents the structural polypeptide of HCV having the amino acid sequence of strain Hutch except wherein amino acid residues 68 to 81 have been substituted by amino acid residues 68 to 81 of the capsid antigen of an HCV genotype 2 isolate. A fourth recombinant HCV capsid antigen is illustrated by SEQ ID NO:14 which represents the structural polypeptide of HCV having the amino acid sequence of strain Hutch except wherein amino acid residues 68 to 81 have been substituted by amino acid residues 68 to 81 of the capsid antigen of an HCV genotype 3 isolate.

Most preferably, DNA segments of this invention which express preferred HCV 1–120 capsid antigens as illustrated in SEQ ID NOS: 8, 10, 12, and 14 have nucleotide sequences represented by SEQ ID NOS:7, 9, 11, and 13 (nucleotides 1 to 378) respectively. Represented in each DNA sequence are the ribosome binding site, coding sequence and stop codon. Nucleotides 212 and 259 are the start of 6 nucleotide recognition sites for the StyI restriction endonuclease.

In a final exemplary embodiment, a DNA segment comprises a nucleotide base sequence that defines an HCV antigen which is a recombinant HCV nonstructural 794 antigen. As exemplified herein, "794 antigen" refers to a recombinant protein with the amino acid sequence set forth in SEQ ID NO:16, which consists of a first 10 amino acid polypeptide region containing a hexahistidine tag (six histidine residues) from amino acid residue 4 to 9, joined by a peptide bond at its carboxy terminus to an NS3 nonstructural antigen (residues 11–115) and a 6 amino acid tail (residues 116 to 121). By NS3 is meant the mature helicase protein of HCV which in strain Hutch corresponds to amino acid residues 1007 to 1615 of the HCV polyprotein. A preferred HCV NS3 nonstructural antigen has the amino acid residue sequence shown in SEQ ID NO:16 from residue 11 to residue 115, which is that of the Hutch strain of HCV (amino acid sequence 1352–1456 of GenBank accession no. M67463).

The hexahistidine sequence present within the first 10 amino acid sequences exemplifies a "Tag" polypeptide designed to facilitate the purification of the composite synthesis product. Following induction and breakage of cells containing vector encoding a protein with a hexahistidine "Tag", the protein of interest can be isolated by metal chelate affinity chromatography in accordance with well established procedures (see, eg. Porath et al. *Nature*, 258 p. 598 (1975)).

In a preferred embodiment, that portion of a recombinant HCV nonstructural 794 antigen encoding DNA segment of this invention that codes for the HCV nonstructural portion has a nucleotide base sequence corresponding to a sequence that codes for an amino acid residue sequence as shown in SEQ ID NO:16 from residue 11 to residue 115 and more preferably has a nucleotide base sequence corresponding to a base sequence shown in SEQ ID NO:15 from base 46 to base 360.

In a more preferred embodiment, a recombinant HCV nonstructural 794 antigen encoding DNA segment codes for an amino acid residue sequence as shown in SEQ ID NO:16 from residue 1 to residue 121. Most preferably, a recombinant HCV nonstructural 794 antigen encoding DNA segment of this invention has a nucleotide base sequence corresponding to the sequence shown in SEQ ID NO:16 from base 1 to base 381.

In preferred embodiments, a DNA segment of the present invention includes its complimentary DNA segment and is preferably bound thereto, thereby forming a double stranded DNA segment. In addition, it should be noted that a double stranded DNA segment of this invention can have a single stranded cohesive tail at one or both of its termini.

A DNA segment of the present invention can easily be prepared from isolated viruses or other sources by the polymerase chain reaction (PCR) or synthesized by chemical techniques, for example, the phosphotriester method of Matteucci et al. *J. Am. Chem. Soc.*, 103:3185 (1981). (the disclosures of the art cited herein are incorporated herein by reference). Of course, by chemically synthesizing the DNA, any desired modification can be made simply by substituting the appropriate bases for those encoding the native amino acid sequence.

The present invention further contemplates a recombinant DNA (rDNA) that includes a DNA segment of the present invention operatively linked to a vector. A preferred rDNA of the present invention is characterized as being capable of directly expressing, in a compatible host, the gene product of interest. By "directly expressing" it is meant that the mature polypeptide chain of the protein is formed by translation alone as opposed to proteolytic cleavage of two or more terminal amino acid residues from a larger translated precursor protein. Preferred rDNAs of the present invention are derivatives of the pGEX7 expression vector containing the DNA segments of the invention.

As used herein, the term "vector" refers to a DNA molecule capable of autonomous replication in a cell and to which another DNA segment can be operatively linked so as to bring about replication or expression of the attached segment. Typical vectors are plasmids, bacteriophage and the like. Vectors capable of directing the expression of a DNA segment of the invention are referred to herein as "expression vectors". Thus, a recombinant DNA molecule (rDNA) is a hybrid DNA molecule comprising at least two nucleotide sequences not normally found together in nature. A vector contemplated by the present invention is also least capable of directing replication, and includes a procaryotic replicon (ori), i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also typically include a gene whose expression confers drug resistance to a bacterial host transformed therewith. Typical bacterial drug resistance genes for use in these vectors are those that confer resistance to ampicillin or tetracycline. Preferred vectors of the present invention also include a procaryotic promoter capable of directing the expression (transcription and translation) of the gene encoding the HIV or HCV antigen or fusion protein in a bacterial host cell, such as E. coli, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. A typical vector is pPL-lambda available from Pharmacia (Piscataway, N.J.).

Although the expression vector pGEX7 has been used as exemplary in producing the proteins described herein, other functionally equivalent expression vectors can be used. Functionally equivalent vectors have the sequence AGGAGGGTTTITCAT to which coding sequences of interest may be joined, and contain an expression promoter that is inducible by any number of methods such as by temperature shift or by addition of IPTG.

A variety of methods have been developed to operatively link DNA segments to vectors via compatible termini. General recombinant DNA technologies are comprehensively described in a plethora of publications, and for experimental protocols, attention is drawn to the treatise by Maniatis et al. (Molecular Cloning: A Laboratory Manual 2nd edition, Cold Spring Harbor Press (1989)), which is incorporated herein by reference.

Synthetic linkers containing one or more restriction sites provide an alternative method of joining the DNA segments to vectors. The DNA segment, generated by endonuclease digestion or, by some alternate procedure such as primer-directed synthesis via techniques such by PCR (see, eg., supra or, more specialized monographs such as M. J. McPherson, P. Quirke and G. R. Taylor (Eds), "PCR. A Practical Approach", IRL Press at Oxford University press, Oxford, UK, (1991)) is treated with bacteriophage T4 DNA polymerase or E. Coli DNA polymerase I, enzymes that remove protruding 3' single stranded termini with the 3'-5' exonucleolytic activities and fill in recessed 3' ends with their polymerizing activities. The combination of these activities therefore generate blunt-ended DNA segments. The blunted segments are then incubated with a large molar excess of linker molecules in the presence of an enzyme that is able to catalyze the ligation of blunt-ended DNA segments, such as the bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment. Synthetic linkers containing a variety of restriction endonuclease sites, as well as the restriction endonucleases themselves are commercially available from a number of sources including New England Biolabs (Boston, Mass.).

Also contemplated by the present invention are RNA equivalents of the above described recombinant DNA molecules.

C. Transformed Cells and Cultures

The present invention also relates to a procaryotic host cell transformed with a recombinant DNA molecule of the present invention, preferably an rDNA capable of expressing a recombinant HIV p24-gp41 fusion protein, a recombinant HCV 1–120 capsid protein, a recombinant HCV CAP-B protein or a recombinant HCV nonstructural antigen 794. Bacterial cells are preferred procaryotic host cells and typically are a strain of E. coli, such as, for example, the E. coli strain W3110 or the strain DH5 available from Bethesda Research Laboratories, Inc., Bethesda, Md. Transformation of appropriate cell hosts with a recombinant DNA molecule of the present invention is accomplished by well known methods that typically depend on the type of vector used. With regard to transformation of procaryotic host cells, see, for example, Cohen et al., Proc. Natl. Acad. Sci. USA, 69:2110 (1972); and Maniatis et al., Molecular Cloning, A Laboratory Manual, Cold Spring Harbor Laboratory, Cold Spring Harbor, N.Y. (1982). Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, J. Mol. Biol., 98:503 (1975) or Berent et al., Biotech., 3:208 (1985). In addition to directly assaying for the presence of rDNA, successful transformation can be confirmed by well known immunological methods when the rDNA is capable of directing the expression of a protein from the inserted gene of interest. Samples of cells suspected of being transformed are harvested and assayed for the presence of the encoded HIV or HCV antigen using antibodies specific for the particular antigen of interest. Such antibodies are well known in the art. Thus, in addition to the transformed host cells themselves, the present invention also contemplates a culture of those cells. Nutrient media useful for culturing transformed host cells are well known in the art and can be obtained from several commercial sources.

D. Methods for Producing Recombinant Proteins and Compositions Containing Same Another aspect of the present invention pertains to a method for producing the HIV and HCV antigens of this invention, more preferably an HIV p24-gp41 fusion protein, an HCV CAP-B protein, an HCV 1–120 capsid protein or an HCV nonstructural antigen 794. The present method entails initiating a culture comprising a nutrient medium containing host cells transformed with a recombinant DNA molecule of the present invention. The culture is maintained for a time period sufficient for the transformed cells to express the HNV or HCV antigen. The expressed protein is then recovered from the culture. However, as is well known in the art, the expressed protein recovered may or may not contain the amino-terminal methionine residue present on the initial translation product depending on cellular processing mechanisms. Methods for recovering an expressed protein from a culture are well known in the art and include fractionation of the protein-containing portion of the culture using well known biochemical techniques. For instance, the methods of gel filtration, gel chromatography, ultrafiltration, electrophoresis, ion exchange, affinity chromatography and the like, such as are known for protein fractionation, can be used to isolate the expressed proteins found in the culture. In addition, immunochemical methods, such as immunoaffinity, immunoadsorption and the like can be performed using well known methods.

E. Recombinant Protein Compositions

In another embodiment, the present invention contemplates a composition containing an HIV or HCV antigen of the invention, including e.g., an HIV p24-gp41 fusion protein, an HCV CAP-B protein, an HCV 1–120 capsid protein or an HCV nonstructural 794 antigen encoded by the DNA segments of the invention or combinations thereof that is essentially free of both procaryotic antigens (i.e. host cell-specific antigens) and other HIV- or HCV-related proteins. By "essentially free" is meant that the ratio of desired HIV or HCV proteins, alone or in combination, to either procaryotic antigen or other HIV- or HCV-related proteins is at least 100:1, and preferably is 1,000:1.

The presence and amount of contaminating protein in a recombinant protein preparation can be determined by well known methods. For example, a sample of the composition is subjected to sodium dodecyl sulfate-polyacrylamide gel electrophoresis (SDS-PAGE) to separate the recombinant protein from any protein contaminants present. The ratio of the amounts of the proteins present in the sample is then determined by densitometric soft laser scanning, as is well known in the art. See Guilian et al., Anal. Biochem., 129:277–287 (1983).

In another embodiment of the invention, the HIV or HCV antigen of the invention is in non-reduced form, e.g., substantially free of sulfhydryl groups because of Cys-Cys bonding that can occur in those antigens having cysteine residues.

G. Diagnostic Systems

A diagnostic system in kit form of the present invention includes, in an amount sufficient for at least one assay, a composition comprising a HIV or HCV antigen of the current invention as a separately packaged reagent. Instructions for use of the packaged reagent are also typically included. "Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, the diagnostic system of the present invention further includes a label or indicating means capable of signaling the formation of a complex containing a recombinant antigen. As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein or polypeptide, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3–46 (1981). The techniques of protein conjugation or coupling through activated functional groups are particularly applicable. See, for example, Avrameas, et al., Scand. J. Immunol., Vol. 8 Suppl. 7:7–23 (1978), Rodwell et al., Biotech., 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself a protein expression product of the present invention. Exemplary specific binding agents are antibody molecules, complement proteins or fragments thereof, protein A, immobilized metal ion chelates, immobilized glutathione and the like. Preferably the specific binding agent can bind the recombinant antigen when the antigen is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of antibodies in a body fluid sample such as serum, plasma or saliva that react with any of the antigens of the present invention. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. Nos. 3,654,090; 3,850,752; and 4,016,043, which are all incorporated herein by reference.

In preferred embodiments, an HIV or HCV antigen of the present invention can be affixed to or coated on a solid matrix to form a solid support that is separately packaged in the subject diagnostic systems. The antigen is typically affixed to the solid matrix by adsorption from an aqueous medium although other modes of affixation, well known to those skilled in the art can be used. Useful solid matrices are well known in the art. Such materials include the cross-linked dextran available under the trademark SEPHADEX from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The HIV or HCV antigen, labeled specific binding agent or amplifying reagent of any diagnostic system described herein can be provided in solution, as a liquid dispersion or in a substantially dry format, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

EXAMPLES

The examples illustrate the present invention but in no way limit its scope.

Example 1

Isolation of the HIV p24 Gene and Construction of Expression Vector

The gag region from the pHXB2CG plasmid clone of HTLV IIIB (obtained from Dr. Robert Gallo, National Cancer Institute, Bethesda, Md.) was isolated by EcoRV restriction enzyme digestion of plasmid pHXB2CG and the resulting 2.86 kilobase fragment was isolated and inserted by ligation into the EcoRV site of a modified pUC8 vector (pUC8NR) to form plasmid pUCGAG (FIG. 1, Step 1).

The plasmid (PUCGAG) was mutagenized to generate an ATG translational initiation codon and an NdeI restriction enzyme site (CATATG) at the beginning of the p24 structural gene by the following series of manipulations (FIG. 1, Step 2). After transformation of pUCGAG into the methylation deficient dam-strain of E. coli, New England Biolabs, a gap was created in the pUCGAG DNA at the p24 amino terminus by cutting with the ClaI and PstI restriction enzymes to form gapped pUCGAG that lacks the smaller DNA segment from the p24 amino terminus. Ten micrograms of gapped pUCGAG DNA and 10 micrograms of pUCGAG DNA cut with the restriction enzyme EcoRI were both subjected to electrophoresis on a 1% agarose gel, and the DNA fragments were each separately isolated from the agarose gel by electroelution (Model 1750 sample concentrator; ISCO, Lincoln, Neb.), combined, extracted twice with a 50/50 mixture of phenol and chloroform, and precipitated with the addition of sodium acetate (final concentration, 100 mM) and three volumes of ethanol.

The precipitated DNAs were collected by centrifugation and resuspended to a concentration of 25 micrograms per milliliter in water. After addition of an equal volume of annealing buffer (80% formamide, 100 mM Tris, pH 8.0, 25 mM EDTA) the resuspended DNAs were denatured by boiling for 5 minutes and allowed to anneal at 37° C. for 30 minutes. The annealed DNAs were diluted with an equal volume of water and precipitated in ethanol as described above to form precipitated annealed DNA.

The NdeI and ATG sequences were joined to the amino terminus of the p24 gene using the following synthetic oligonucleotide:
5'-CCAAAATTACCATATGCCAATCGTGCAGAAC-3' (SEQ ID NO:19) The 10 nucleotides at the 5' end and 9 nucleotides at the 3' end of this oligonucleotide are homologous to the HTLV IIIB DNA sequence (University of Wisconsin genetic database). The intervening nucleotides were chosen to minimize the formation of secondary structures within the oligonucleotide and within the RNA expected to be generated from this sequence during expression of these sequences in E. coli.

Forty picomoles of the above oligonucleotide (synthesized on a Pharmacia Gene Assembler) was phosphorylated (as described in Molecular Cloning by T. Maniatis, E. F. Fritsch and J. Sambrook, Cold Spring Harbor Laboratory, 1982, p. 125) and admixed with 2.5 micrograms of the precipitated annealed DNA described above. The admixed DNAs were then annealed by heating the admixture to 65° C. for 5 minutes and then cooling to room temperature over the course of an hour in ligase buffer (op. cit., p.474). The resulting DNA molecule (i.e., a gapped template) containing the precipitated annealed DNA described above and the gapped template with the annealed oligonucleotide was then repaired in vitro in ligase buffer by incubating for 3 hours at 15° C. in the presence of 25 $\mu$M of each deoxynucleoside triphosphate, 50 $\mu$M adenosine triphosphate, 5 units of T4 DNA ligase and 1 unit of the Klenow fragment of E. coli DNA polymerase.

After transformation into competent cells of the JM83 strain of E coli the bacterial colonies were screened by hybridization with radiolabelled oligonucleotide on nitrocellulose (op. cit., pp.250–251, 313–329). A single colony was isolated by this procedure containing the plasmid pUCp40 (FIG. 1), with the DNA sequence for the amino terminal sequence of the p24 gene as disclosed in U.S. Pat. No. 5,470,720.

The DNA fragment from pUCp40 encoding a p24-p 15 fusion protein referred to as p40 below and located between the NdeI restriction enzyme site created by the above mutagenesis and the EcoRV site, was isolated by digesting plasmid pUCp40 with NdeI and EcoRV followed by separation on an agarose gel, extraction and precipitation of the separated fragment.

Plasmid pGEX7 DNA was linearized by digestion with NdeI and EcoRV. Plasmid pGEX7 is a bacterial expression vector deposited as plasmid PHAGE 38 with the American Type Culture Collection (ATCC) on Jun. 9, 1988 and given the ATCC accession number 40464. It contains a lambda bacteriophage promoter ($P_L$), the gene for its temperature sensitive repressor (cI857), the sequence AGGAAGGGTTTTTCAT and an origin of replication (ori).

The digestion of pGEX7 with NdeI and EcoRV results in the production of two linear fragments, one of which contains the amp$^r$ and cI857 genes and the origin of replication and has NdeI and EcoRV cohesive termini. The above described p40 gene-containing NdeI/EcoRV restriction fragment of pUCp40 was then ligated to the pGEX7 NdeI/EcoRV amp$^r$ gene-containing fragment via their respective NdeI and EcoRV termini to form the plasmid pGEXp40 (FIG. 1, Step 3).

The sequences of pGEXp40 encoding p15 were removed from plasmid pGEXp40 by restriction digestion with the enzymes PpuMI and BamHI. Thereafter the 3' end of the p24 gene was reconstructed as indicated by FIG. 1, Step 4 by synthesizing two complementary oligonucleotides (SEQ ID NO:20 and SEQ ID NO:21) which when annealed form a duplex comprising translational stop codons and overhanging ends corresponding to PpuMI and BamHI restriction enzyme sites. The resulting rDNA plasmid, pGEXp24, expresses an HIV p24 antigen.

Example 2

Formation of Composite DNAs Comprising the pGEXp24 Vector With an Inserted Gene for a Conserved Envelope gp41 (Subtype 0) Antigen.

The plasmid pGEXp24, was linearized by digestion with the restriction enzyme PpuMI and purified by phenol-chloroform extraction followed by precipitation with ethanol. Two complementary oligonucleotides (sequences given by nucleotides 686 to 763 and the complement of nucleotides 689 to 766 of SEQ ID NO:1) forming protruding cohesive termini when annealed, were synthesized. The synthetic oligonucleotides were allowed to form a duplex by mixing and heating to 90° C. for a approximately 3 minutes, followed by annealing at room temperature for a period of 10 minutes. The hybrid molecule represents a hybrid gene sequence encoding the p24 molecule interrupted after codon 225 by a linker amino acid (lysine), envelope sequence (amino acids 227–249) for the conserved region of HIV Subtytpe 0 gp41 polypeptide, strain ANT, followed by a repetition of p24 residues 224 and 225 and then p24 residues 226–232.

A similar hybrid oligonucleotide representing the gp41 conserved region of HIV Subtype 0, strain MVP 5180, was formed by synthesizing complementary oligonucleotides with the sequences given by nucleotides 686 to 763 and the complement of nucleotides 689 to 766 of SEQ ID NO:3.

A third hybrid oligonucleotide representing the gp41 conserved region of HIV Subtype 0, strain GenBank X84328 was formed by synthesizing complementary oligonucleotides with the sequences given by nucleotides 686 to 763 and the complement of nucleotides 689 to 766 of SEQ ID NO:5.

All three duplexes were separately mixed with the linearized pGEXp24 vector and 400 U of T4 ligase and incubated in ligase buffer containing 1 mM ATP at 16° C. overnight. Subsequent transformation into competent *E. coli* and screening of mini-preparations by AvaII digestion allowed for the selection of clones containing the insert as described in U.S. Pat. No. 5,470,720. Mini-inductions confirmed high level synthesis of the gene product of interest, as evidenced by lysing induced cultures in the presence of SDS and running the lysate on a 16% SDS PAGE. The plasmid containing the hybrid gene formed by the first oligonucleotide pair, designated pGEXp24gp41-ANT, comprises the nucleotide sequence given by SEQ ID NO:1. The plasmid containing the hybrid gene formed by the second oligonucleotide pair, designated pGEXp24gp41-MVP, comprises the nucleotide sequence given by SEQ ID NO:3. The plasmid containing the hybrid gene formed by the third oligonucleotide pair, designated pGEXp24gp41-X84328, comprises the nucleotide sequence given by SEQ ID NO:5.

Example 3

Purification of Recombinant p24-gp41 (subtype 0) Fusion Proteins

Plasmids containing the lambda promoter (pL) are normally carried in a strain of bacteria containing a lysogen of bacteriophage lambda in order to minimize the expression of the gene product of interest during the manipulation of DNAs. The pGEX7-based plasmids described in Example 1 were all carried in a lysogen of the MM294 strain of *E. coli*. Expression from the lambda promoter of pGEX7 can be demonstrated by transfer of the plasmid into an uninfected bacterial host (e.g., *E. coli* strain W3110, accession no. #27325, ATCC, Rockville, Md.) and inactivation of the cI repressor protein at 42° C. Competent *E. coli* (strain W3110, 100 μl bacterial suspension) were transformed with 1 μl of pGEXp24gp41-ANT, pGEXp24gp41-MVP or pGEXp24gp41-X84328. After 60 minutes on ice, the bacteria were diluted to 1 ml with LB medium and incubated for a further 60 minutes at 30° C. Aliquots of the culture were than plated on ampicillin containing agar plates which were held at 30° C. for at least 24 hours. A colony was picked and inoculated into 5 ml of LB medium and incubated for approximately 6 hours at 30° C. 1 ml of the growing culture, indicated by developing turbidity of the inoculum, was then transferred to a 1 liter flask for further overnight culture, using a temperature controlled shaker at 300 rpm. The main culture was initiated the following morning by inoculating each of 6 flasks containing 0.9 liter of LB Medium and 50 mg ampicillin/liter with 100 ml of the overnight culture. The flasks were shaken at 350 rpm for 1.5 hours. The cultures were induced by raising the temperature to 42° C. and maintained at that temperature for 4 hours. The cells were harvested by centrifugation (Sorvall, GSA Rotor, 7,000 rpm, 10 minutes in the cold), transferred to a storage container and typically stored frozen until used for purification.

The cell paste from 6 liter cultures (approximately 30 g of frozen bacteria) were thawed and suspended in an equal volume of 0.2 M phosphate buffer, pH 7.0, containing 10 mM EDTA and 10 mM benzamidine. Lysozyme (1 mg/g cell paste) and PMSF (0.2 mg/g cell paste) was added and the suspension stirred for approximately 30 minutes at room temperature. During this period, the material became very viscous. The cells were then placed in an ice bath and subjected to 3 minutes of sonication on ice with intervening cooling periods of 1–2 minutes.

Soluble materials were removed by centrifugation (Sorvall, SS-34 rotor, 20,000 rpm for 30 minutes) and the extraction procedure was repeated using 0.2 M phosphate buffer containing 10 mM EDTA and 10 mM benzamidine. The combined supernatants were discarded and the sediment suspended in 6 M urea containing 0.02 M Tris-HCl buffer, pH 8.6. The suspension was subjected to a further cycle of sonication on ice (60 seconds) and the centrifugation was repeated. The supernatant was saved and the sediment re-extracted once, using urea-tris buffer of the same composition. The combined supernatants were treated with ammonium sulfate (0.3 g/ml of solution), kept at 4° C. for about 30 minutes and then centrifuged as X described above. A large precipitate had formed which was dissolved in approximately 20 ml of 6 M Guanidine-HCl, containing 0.1 M phosphate buffer, 5 mM EDTA, pH 7.0. The solubilized material was clarified by renewed centrifugation and then applied to a 5×105 cm column, containing Sepharose S-300 gel and equilibrated with 6 M Guanidine-HCl in 0.1 M phosphate-5 mM EDTA buffer, pH 7.0. Fractions (10 ml) were eluted and, following dialysis against 6 M urea of selected aliquots, analyzed by SDS gel electrophoresis. Based on the gel pattern, appropriate fractions containing gene products migrating to a position of the gel which corresponded to that reference proteins, or, if such was unavailable, similar to the band appearing as a consequence of the induction of cultures carrying the expression vector, were pooled and exhaustively dialyzed against 4 M urea containing 0.015 M Tris-HCl buffer, pH 8.6.

Figures 1, 2:
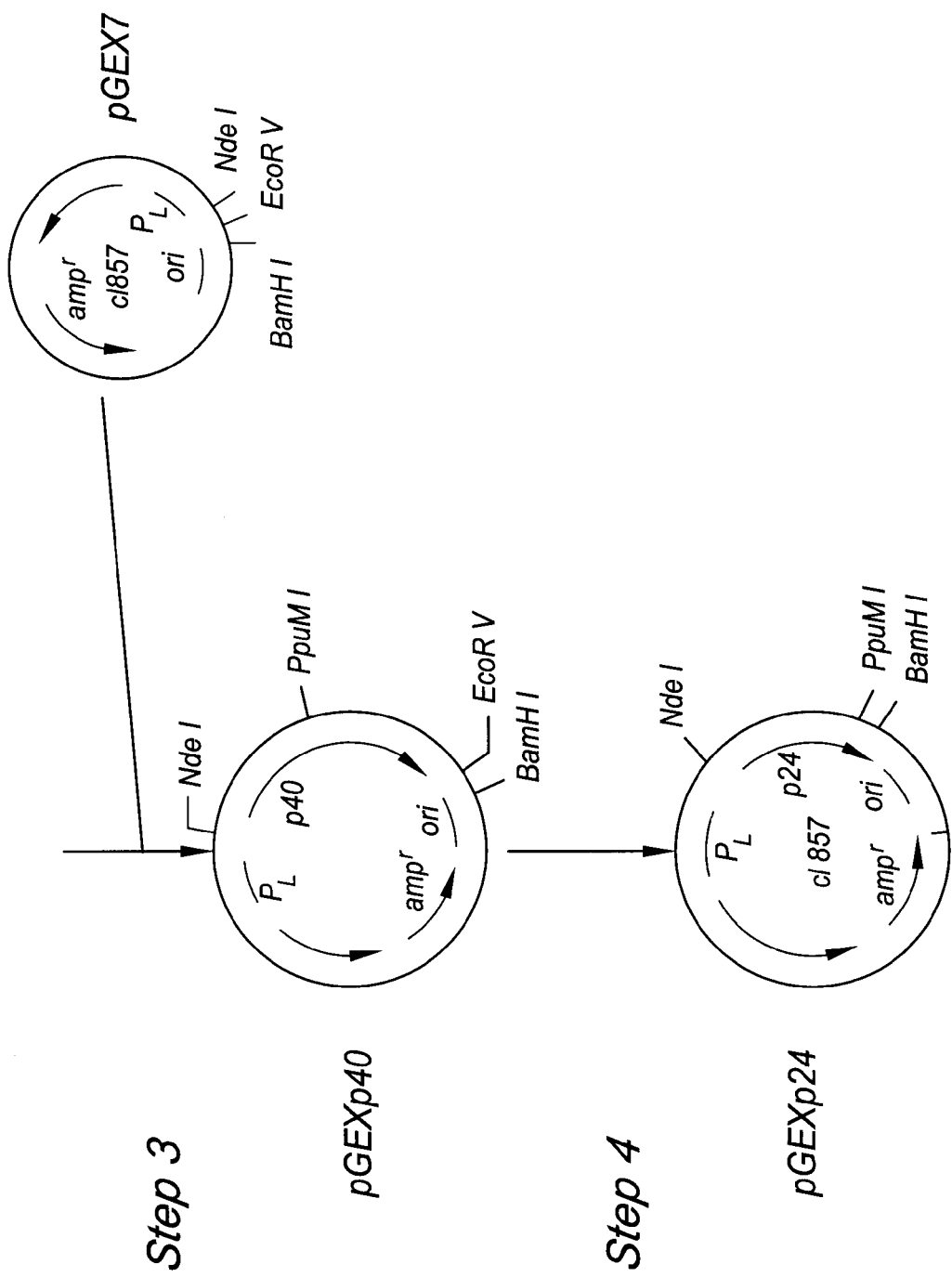
FIG. 2 illustrates the HIV p24-gp41 hybrid proteins obtained after purification from induced bacterial cultures previously transformed with pGEXp24gp41 of U.S. Pat. No. 5,470,720 or with pGEXp24gp41-ANT, pGEXp24gp41-MVP or pGEXp24gp41-X84328 of the present invention.
Figure 2:
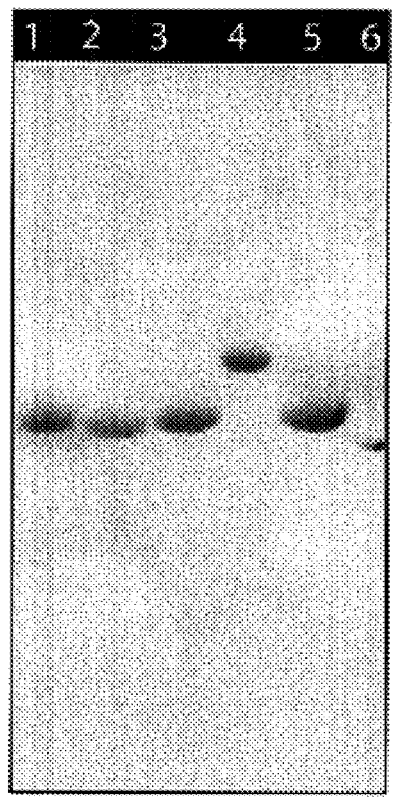
Figure 3:
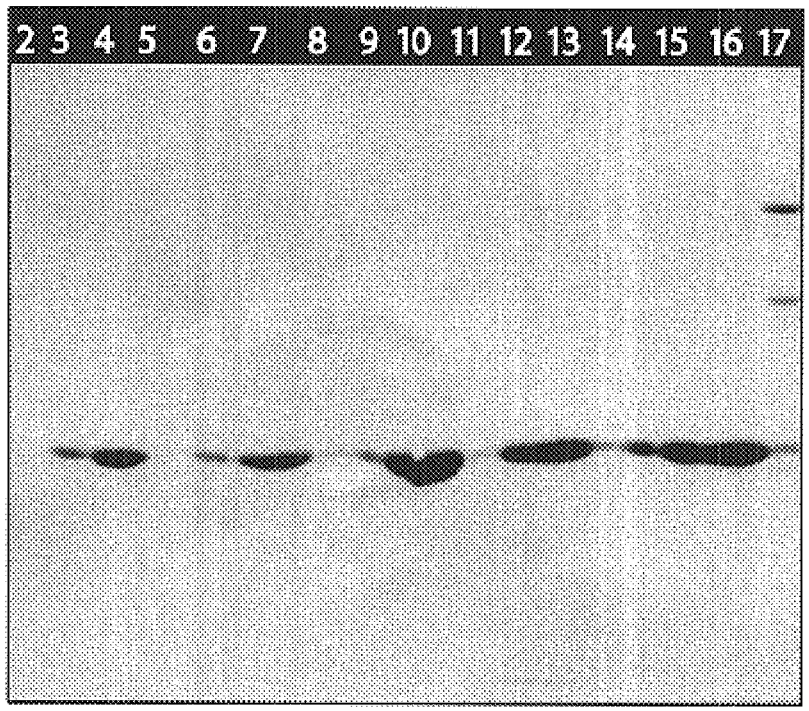
FIG. 3 illustrates the HCV 1–120 capsid antigen (strain Hutch) with an amino acid substitution of valine for alanine at residue 68 after purification from induced bacterial cultures previously transformed with pGEX-C120H-V68 of the present invention.
Figure 4:
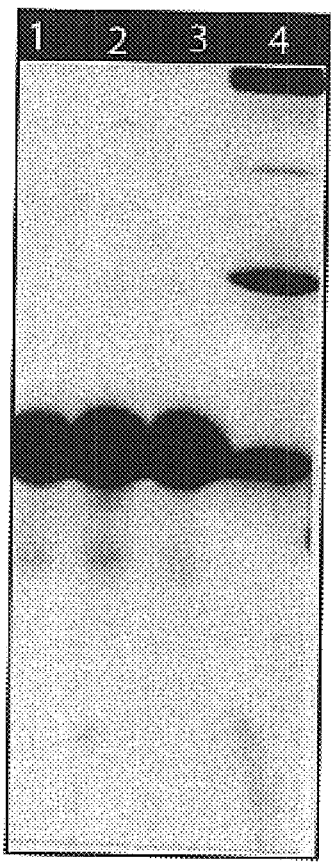
FIG. 4 illustrates the HCV NS3-794 antigen (strain Hutch) after purification from induced bacterial cultures previously transformed with pGEX7-NS3-794 of the present invention.

The dialyzed, clear solution was applied to a column (2.5×30 cm) of DEAE-Sepharose equilibrated with 4 M urea-0.015 M Tris-HCl buffer, pH 8.6. Following application of the sample and washing to remove non-bound constituents, the protein of interest was eluted with a salt gradient (250×250 ml, 0–0.1 M NaCl in the initial Tris-HCl buffer containing 4 M urea) and monitored by analysis in 16% SDS PAGE. Fractions containing the protein of interest were pooled and adjusted to pH 5.6 by addition of glacial acetic acid. The pH-adjusted pooled material was then applied to a column (2.5×20 cm) of CM Sepharose equilibrated with 20 mM sodium acetate buffer, pH 5.6 containing 4 M urea. A salt gradient (250×250 ml, 0–0.4M NaCl in the same urea-containing acetate buffer) was applied and fractions were collected. Fractions were again analyzed for the protein of interest. These fractions containing purified protein were pooled and stored at frozen at −20° C. FIG. 2 shows an analytical SDS gel of the three recombinant p24-gp41 hybrid proteins of subtype O after being purified in accordance with the above protocol.

Figure 5:
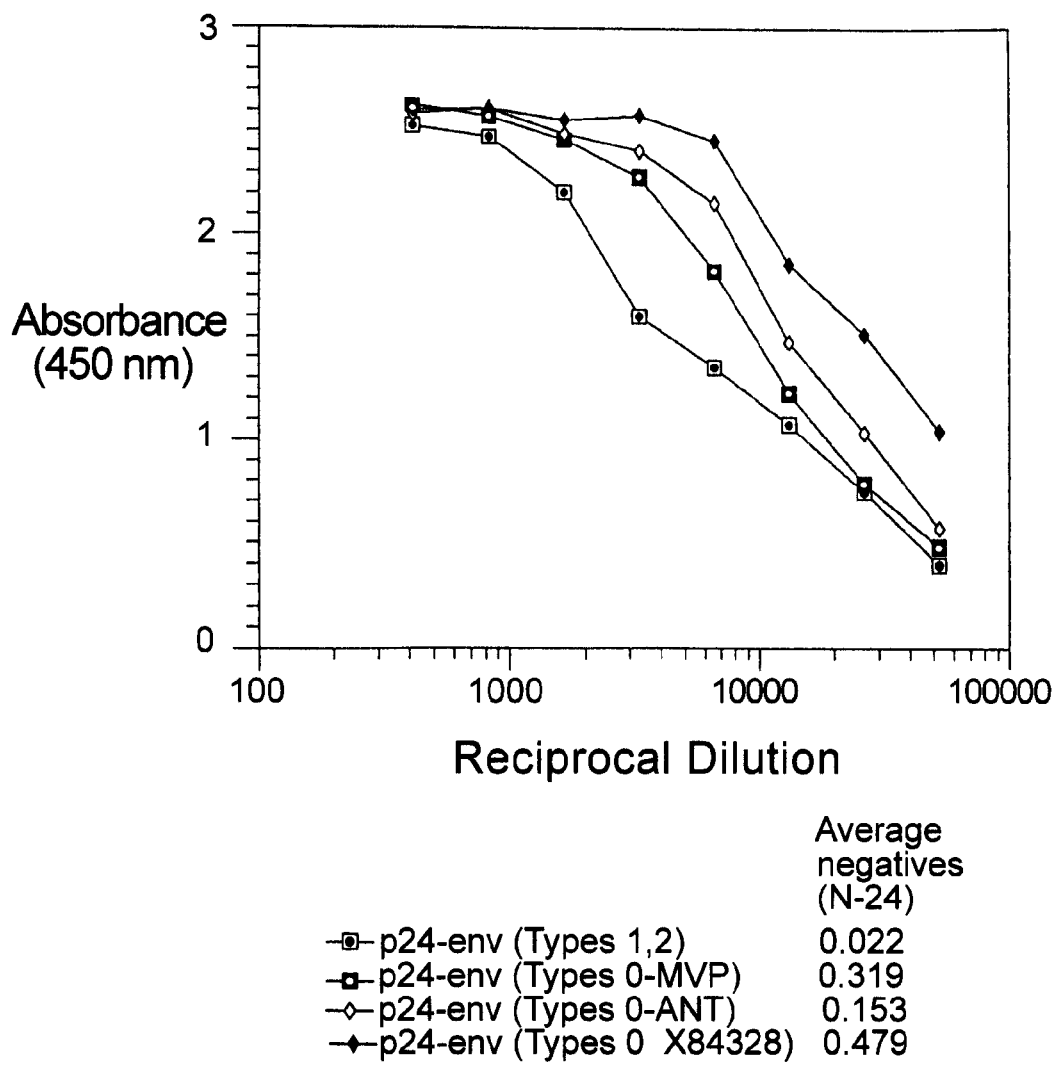
FIG. 5 illustrates ELISAs of serially diluted HIV positive antiserum using polystyrene plates coated with (A) p24-gp41 recombinant protein of U.S. Pat. No. 5,470,720; (B) p24-gp41 Subtype O ANT recombinant protein; (C) p24-gp41 Subtype O MVP5180 recombinant protein; and (D) p24-gp41 Subtype O X84328 recombinant protein.
Figure 6:
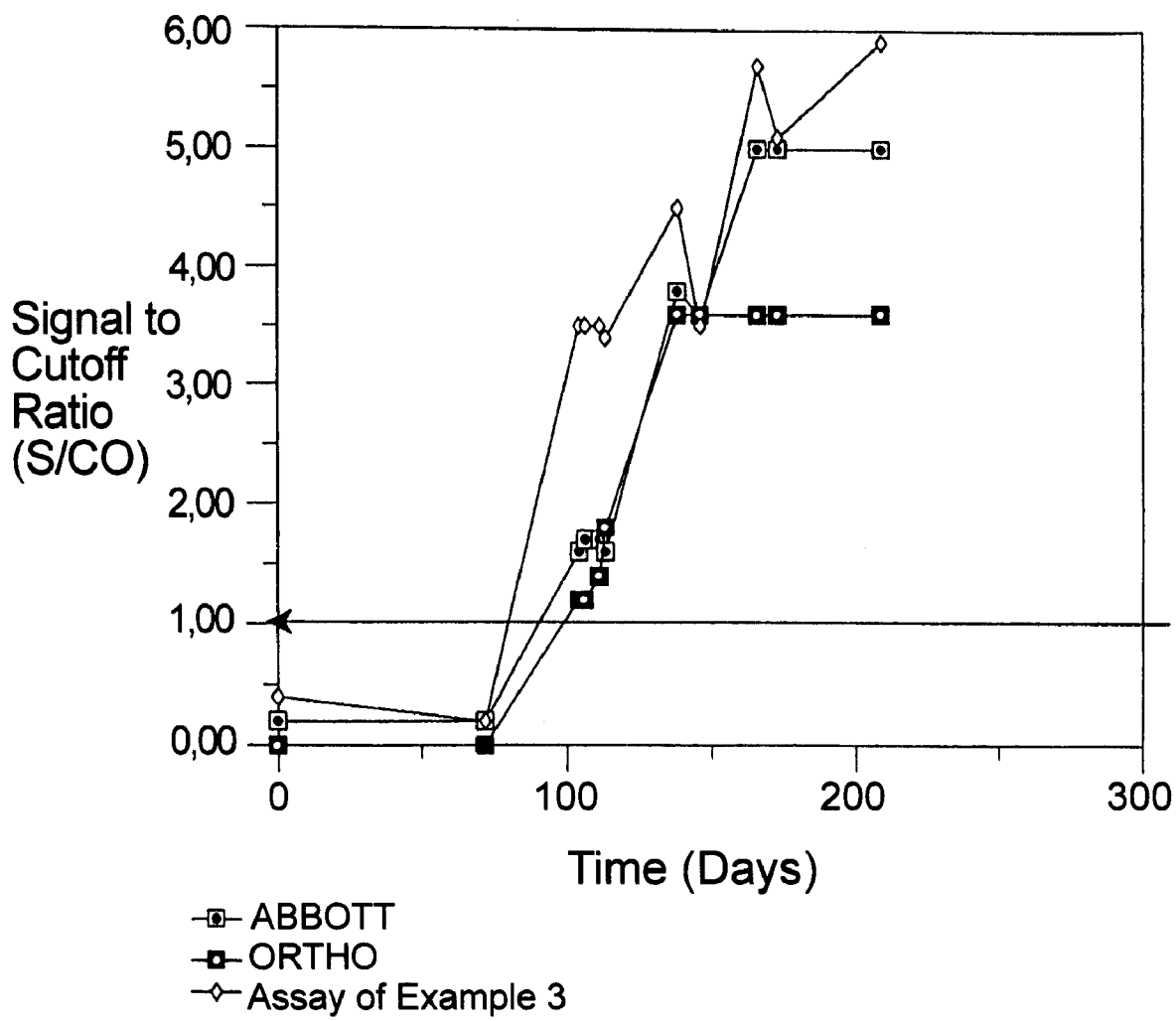
FIG. 6 illustrates the immune reactivity in an ELISA of a combination of the recombinant proteins of FIGS. 3 and 4 with the well-characterized, commercially available Boston Biomedica PHV901 seroconverter serum from an individual who developed HCV infection.
Figure 7:
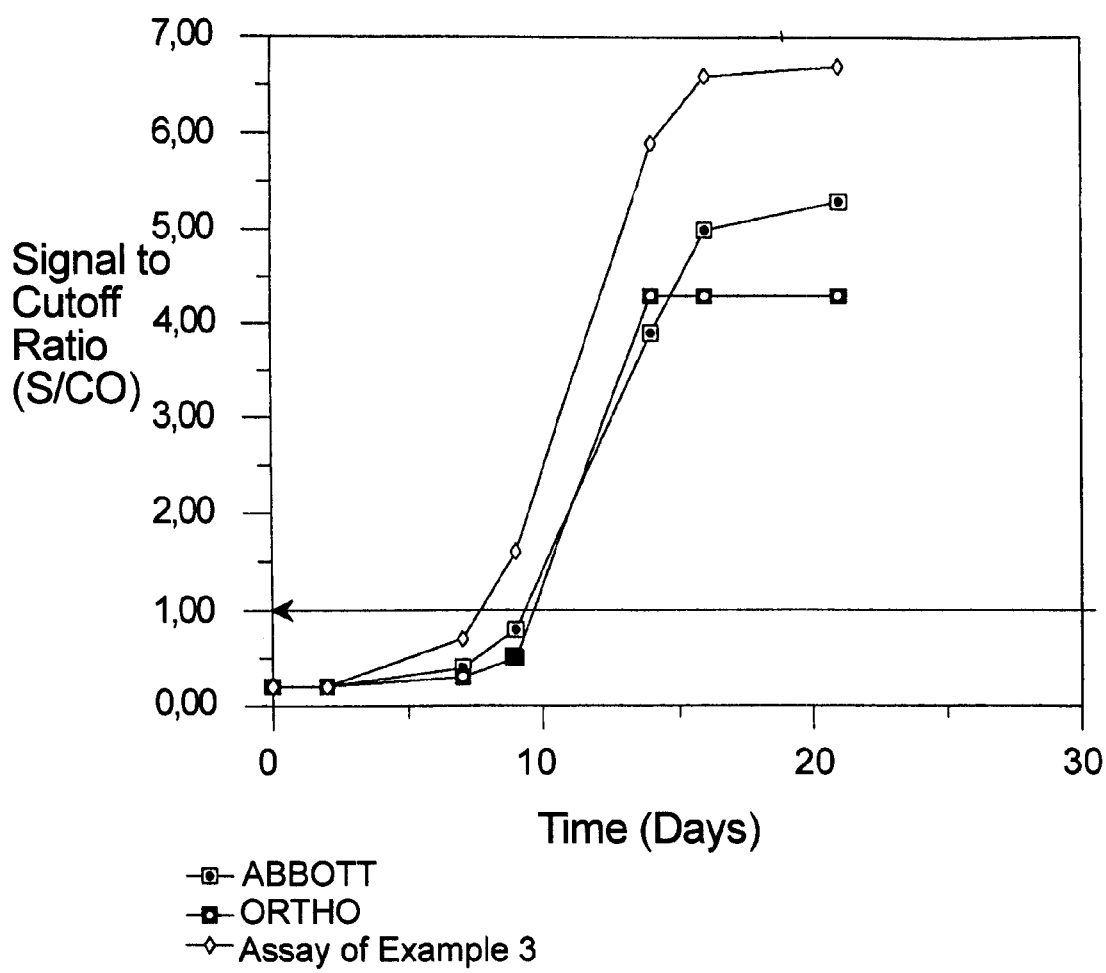
FIG. 7 illustrates the immune reactivity in an ELISA of a combination of the recombinant proteins of FIGS. 3 and 4 with the well-characterized, commercially available Boston Biomedica PHV902 seroconverter serum from an individual who developed HCV infection.
Figure 8:
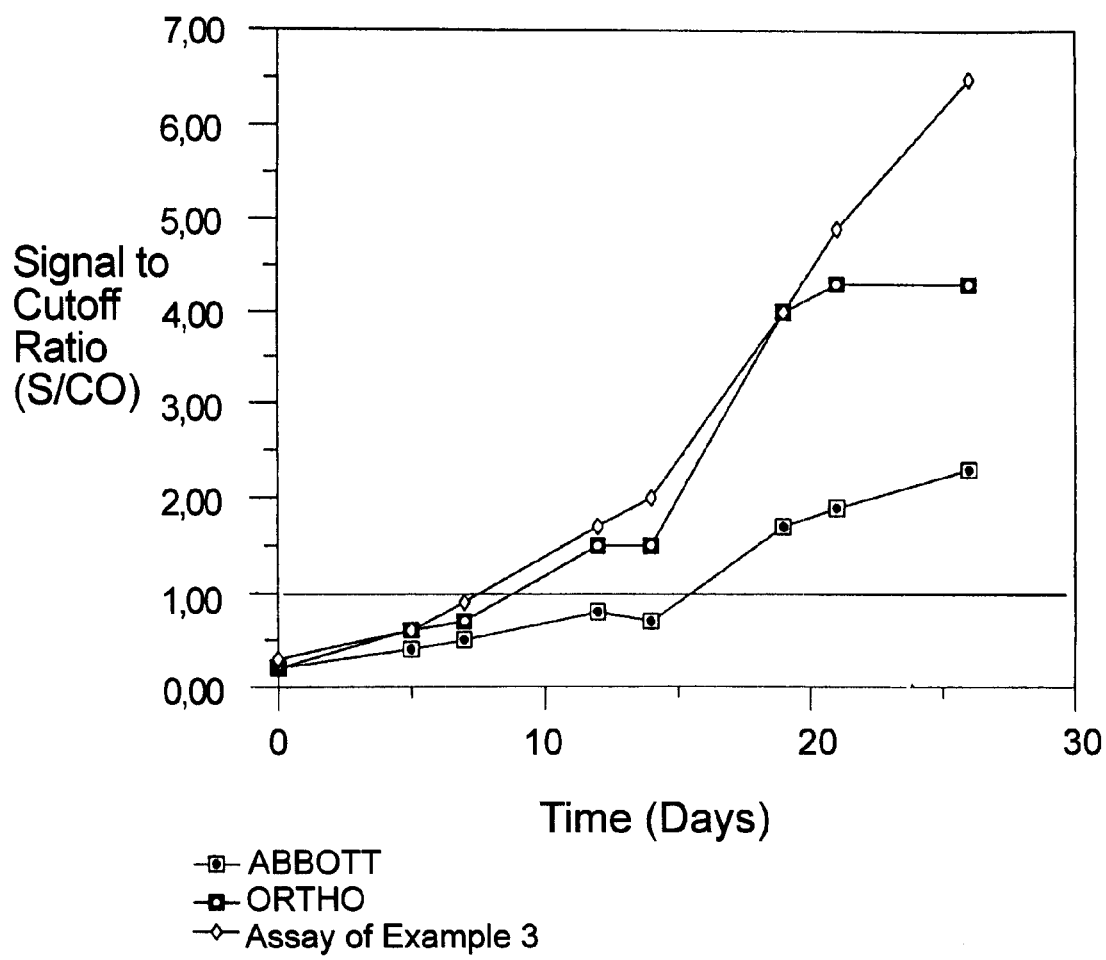
FIG. 8 illustrates the immune reactivity in an ELISA of a combination of the recombinant proteins of FIGS. 3 and 4 with the well-characterized, commercially available Boston Biomedica PHV903 seroconverter serum from an individual who developed HCV infection.

To test for immune reactivity with HIV positive sera, polystyrene wells (Nunc, Polysorp) were coated with mixtures of the p24-gp41 hybrid proteins described above in concentrations of 1 µg/ml for 16 hours at 4° C. After blocking with 3% bovine serum albumin overnight, the plates were dried under vacuum and then used to analyze the immune reactivity against sequential dilutions of a serum known to test positive for HIV antibody. FIG. 5 shows a titration curve using the three newly synthesized antigens in comparison with the prototype gene product obtained from pGEXp24-gp41 as disclosed in U.S. Pat. No. 5,470,720. The three antigens produce strong immune reactivity with this serum, comparable to that seen with the reference protein.

Example 4

Formation of a Recombinant HCV Capsid Protein Gene Joined to pGEX7 for Synthesis of Carrier-free Polypeptide.

A. Isolation of HCV Clones and Sequence Analysis (1) Isolation of HCV RNA and Preparation of cDNA As a source for HCV virions, blood was collected from a chimpanzee infected with the Hutchinson (Hutch) strain exhibiting acute phase HCV. Plasma was clarified by centrifugation and filtration. Virions were then isolated from the clarified plasma by immunoaffinity chromatography on a column of HCV IgG (Hutch strain) coupled to protein G sepharose. HCV RNA was eluted from the sepharose beads by soaking in guanidinium thiocyanate and the eluted RNA was then concentrated through a cesium chloride (CsCl) cushion. Maniatis et al., Molecular Cloning: A Laboratory Manual, Maniatis et al., eds. Cold Spring Harbor, N.Y. (1989).

The purified HCV RNA was used as a template in a primer extension reaction admixture containing random and oligo dT primers, dNTP's, and reverse transcriptase to form first strand cDNAs. The resultant first strand cDNAs were used as templates for synthesis of second strand cDNAs in a reaction admixture containing DNA polymerase I and RNAse H to form double stranded (ds) cDNAs (Maniatis et al., supra). The synthesized ds cDNAs were amplified using an asymmetric synthetic primer-adaptor system wherein sense and anti-sense primers were annealed to each other and ligated to the ends of the double stranded HCV cDNAs with T4 ligase under blunt-end conditions to form cDNA-adaptor molecules. Polymerase chain reaction (PCR) amplification was performed by admixing the cDNA-adaptor molecules with the same positive sense adaptor primers, dNTP's and TAQ polymerase to prepare amplified HCV cDNAs. The resultant amplified HCV cDNA sequences were then used as templates for subsequent amplification in a PCR reaction with specific HCV oligonucleotide primers.

(2) Synthesis of Oliponucleotides For Use in HCV Cloning

Oligonucleotides were selected to Correspond to the 5' sequence of Hepatitis C virus which encodes the HCV structural capsid and envelope proteins (HCJ1 sequence: Okamoto et al., *Jap. J. Exp. Med.*, 60:167–177, 1990). The selected oligonucleotides were synthesized on a Pharmacia Gene Assembler according to the manufacturer's instruction, purified by polyacrylamide gel electrophoresis.

(3) PCR Amplification of HCV cDNA

PCR amplification was performed by admixing the primer-adapted amplified cDNA sequences prepared in Example 4.A.(1) with the synthetic oligonucleotide primer pair 690:694. (690: nucleotides 16–36 of SEQ ID NO:9; 694: complement of nucleotides 162–178 of SEQ ID NO:9). The resulting PCR reaction admixture contained the primer-adapted amplified cDNA template, oligonucleotides 690 and 694, dNTP's, salts (KC1 and $MgCl_2$) and TAQ polymerase. PCR amplification of the cDNA was conducted by maintaining the admixture at a 37° C. annealing temperature for 30 cycles. Aliquots of samples from the first round of amplification were reamplified at a 55° C. annealing temperature for 30 cycles under similar conditions.

(4) Preparation of Vectors Containing PCR Amplified ds DNA

Aliquots from the second round of PCR amplification were subjected to electrophoresis on a 5% acrylamide gel. After separation of the PCR reaction products, the region of the gel containing DNA fragments corresponding to the expected 690:694 amplified product of approximately 224 bp was excised and purified following standard electroelution techniques (Maniatis et al., supra). The purified fragments were kinased and cloned into the pUC 18 plasmid cloning vector at the SmaI polylinker site to form a plasmid containing the DNA segment 690:694 joined to pUC18.

The resulting mixture containing pUC 18 and a DNA segment corresponding to the 690:694 sequence region was then transformed into the *E. coli* strain JM83. Plasmids containing inserts were identified as lac-(white) colonies on X-gal medium containing ampicillin. pUC18 plasmids which contained the 690:694 DNA segment were identified by restriction enzyme analysis and subsequent electrophoresis on agarose gels, and were designated pUC18 690:694.

(5) Sequencing of HCV Clones that Encode the Putative Capsid Protein

Two independent colonies believed to contain a pUC 18 vector having the HCV Hutch strain 690:694 DNA segment (pUC18-690:694) that codes for the amino terminus of the capsid protein were amplified and used to prepare plasmid DNA by CsCl density gradient centrifugation by standard procedures (Maniatis et al., supra). The plasmids were sequenced using $^{35}S$ dideoxy procedures with pUC 18 specific primers. The two plasmids were independently sequenced on both DNA strands to assure the accuracy of the sequence.

(6) Preparation of HCV Clones from the 5' End of the Genome

To obtain a clone encoding the remainder of the of the HCV Hutch capsid region (Okamoto et al., supra), the oligonucleotide pair 693:691 (693: nucleotides 162–178 of SEQ ID NO:9; 691: complement of nucleotides 355–375 of SEQ ID NO:9) were used in PCR reactions. cDNA was prepared as described in Example 4.A.(1) from viral HCV RNA (Hutch) and used in PCR amplification as described in Example 4.A.(3) with the oligonucleotide pair 693:691. The resultant PCR amplified ds DNA was then cloned into pUC 18 cloning vectors and screened for inserts as described in Example 4.A.(4) to form pUC18–693:691. Clones were then sequenced with pUC 18 specific primers as described in Example 4.A.(5). Plasmid pUC18-693:691 was found to contain a HCV DNA segment that is 157 bp in length and corresponds to the HCV prototype HJC1 sequence (SEQ ID NO:9) from nucleotides 218–375.

B. Production of Recombinant DNA (rDNA) Encoding Fusion Proteins (1) Introduction of the 690:694 Fragment into pGEX-3X for Expression of GST Fusion Protein The pUC18-690:694 DNA was subjected to restriction enzyme digestion with EcoRI and BamHI to release a DNA segment containing the HCV 690:694 fragment. The released DNA segment was subjected to acrylamide electrophoresis and a DNA segment containing the 224 bp HCV insert plus portions of the pUC 18 polylinker was then excised and eluted from the gel as described in Example 4.A.(4). The DNA segment was extracted with a mixture of phenol and chloroform, and precipitated.

The precipitated DNA segment was resuspended to a concentration of 25 µg/ml in water and treated with the Klenow fragment of DNA polymerase to fill in the staggered ends created by the restriction digestion. The resultant blunt-ended 690:694 containing segment was admixed with the bacterial expression vector pGEX-3X, (Pharmacia Inc., Piscataway, N.J.) which was linearized with the blunt end restriction enzyme SmaI. The admixed DNAs were then ligated by maintaining the admixture overnight at 16° C. in the presence of ligase buffer and 5 units of T4 DNA ligase to form a plasmid of 690:694 DNA segment joined to pGEX-3X.

(2) Selection and Verification of Correct Orientation of Ligated Insert

The ligation mixture containing the pGEX-3X vector and the 690:694 DNA containing segment was transformed into host *E. coli* strain W3110. Plasmids containing inserts were identified by selection of host bacteria containing vector in Luria broth (LB) media containing ampicillin. Bacterial cultures at stationary phase were subjected to alkaline lysis protocols to form a crude DNA preparation. To screen for a vector containing the 690:694 DNA segment, plasmid DNA was digested with the restriction enzyme XhoI, which cleaves within the 690:694 DNA segment, but not within the pGEX-3X vector.

Several 690:694 DNA segment-containing vectors were amplified and the resultant amplified vector DNA was purified by CsCl density gradient centrifugation. The DNA was sequenced across the inserted DNA segment ligation junctions by $^{35}$S dideoxy methods with a primer which hybridized to the pGEX-3X. Vectors containing 690:694 DNA segment having the correct coding sequence for in-frame translation of an HCV structural protein were thus identified and selected to form pGEX-3X-690:694.

(3) Structure of the Fusion Protein

The pGEX-3X vector is constructed to allow for inserts to be placed at the C terminus of Sj26, a 26-kDa glutathione-S-transferase (GST; EC 2.5.1.18) encoded by the parasitic helminth *Schistosoma japonicum*. The insertion of the 690:694 HCV fragment in-frame behind Sj26 allows for the synthesis of the Sj26-HCV fusion polypeptide. The HCV polypeptide can be cleaved from the GST carrier by digestion with the site-specific protease factor Xa (Smith et al., *Gene*, 67:3140, 1988).

The resulting rDNA molecule, pGEX-3X-690:694, encodes an HCV fusion protein having an amino terminal polypeptide portion corresponding to residues 1 to 221 of GST, a four residue intermediate portion defining a cleavage site for the protease Factor Xa, a nine residue linker, a polypeptide portion corresponding to amino acid residue sequence 1 to 74 of SEQ ID NO:9 and a six residue tail.

(4) Introduction of the 690:694 Fragment into pGEX-3X

Plasmid pGEX-3X-693:691 was formed by first subjecting the plasmid pUC18-693:691 prepared in Example 4.A.(6) to restriction enzyme digestion with EcoRI and BamHI as in Example 4.B.(I). The purified DNA segment was admixed with and ligated to the pGEX-3X vector which was linearized by restriction enzyme digestion with EcoRI and BamHI in the presence of T4 ligase at 16° C. to form the plasmid pGEX-3X-693:691.

A pGEX-3X plasmid containing a 693:691 DNA segment was identified as in Example 4.B.(2) with the exception that crude DNA preparations were digested with EcoRI and BamHI to release the 693:691 insert. A pGEX-3X vector containing a 693:691 DNA segment having the correct coding sequence for in-frame translation of an HCV structural protein was identified by sequence analysis as performed in Example 4.B.(2) and selected to form pGEX-3X-693:691.

The resulting vector encodes a fusion protein (GST:HCV 693:691) that is comprised of an amino-terminal polypeptide portion corresponding to residues 1–221 of GST, an intermediate polypeptide portion corresponding to residues 222–225 and defining a cleavage site for the protease Factor Xa, a five residue linker portion, a carboxy-terminal polypeptide portion corresponding to amino acid residues 69 to 120 of the HCV capsid antigen, and a three residue tail.

C. Plasmids Encoding Complete Capsid Proteins (1) Construction of a Vector Expressing a Composite Gene To generate a composite gene spanning the entire amino acid region of 1–120 and to create an operative linkage of the gene to the first. DNA segment of this invention,(i.e., AGGAGGGTTTTTCAT), the following experiments were conducted. The above described plasmids pGEX-3X-690:694 and pGEX-3X-691:693, containing base pairs 1–224 and 203–360, respectively, of an HCV capsid gene (U.S. Ser. No. 07/573,643) were used as target templates for each of two separate PCR reactions encompassing the following primer pairs.

A first PCR reaction was performed using a primer pair with sequences given by SEQ ID NO:22 and the complement of nucleotides 219–239 of SEQ ID NO:7 to amplify a 210 base pair fragment from plasmid pGEX-3X-690:694. The amplified fragment contains a single NdeI and EagI site at the 5' and 3' ends, respectively.

A second PCR reaction was performed using a primer pair (sequences given by SEQ ID NO:23 and nucleotides 219 to 239 of SEQ ID NO:7) to amplify a 150 bp fragment from plasmid pGEX-3X-691:693. The second amplified fragment contains an EagI site at the 5' end and an EcoRI site at the 3' of the amplimer.

The PCR products were cut with the NdeI and EagI (first PCR reaction product) and with EagI and EcoRI (second PCR reaction product). In a third digestion, the pGEX7 vector was digested with NdeI and EcoRI. Following isolation by preparative electrophoresis in 5% acrylamide of each DNA segment, a three-way ligation mixture containing the isolated and restricted PCR reaction products and isolated pGEX7 vector was formed, and allowed to incubate with T4 Ligase overnight at 16° C. The mixture was then transformed into competent cells, colonies were selected for plasmid mini-preparations and subsequently analyzed by redigestion with NdeI and EcoRI. The vector pGEX-C120H-V68 released an insert of the proper length upon restriction digestion with NdeI and EcoRI and had the nucleotide sequence shown in SEQ ID NO: 7. Compared with the sequence for the HUTCH strain, pGEX-C120H-V68 has amino acid substitutions at amino acid 4 (Ile instead of Asn) and amino acid 68 (Val instead of ala) shown in SEQ ID NO: 8.

(2) Vectors Expressing Modified Capsid Proteins

The codon at position 68 is included in a stretch of the DNA molecule spanned by two StyI sites, (nucleotides 212 and 259 of SEQ ID NO:7 are the first base in the StyI recognition sites). A plasmid vector containing the HUTCH sequence in this StyI fragment is made by ligating a DNA fragment formed by annealing complementary synthetic oligonucleotides with sequences given by nucleotides 213 to 259 and the complement of nucleotides 217 to 263 of SEQ ID NO: 9 into the StyI-digested pGEX-C120H-V68 vector. The proper orientation of the inserted DNA fragment is assured as the two StyI cohesive ends are different. The sequence of the resulting vector, pGEX-C120H, codes for alanine at amino acid 68 of the capsid sequence (SEQ ID NO:10).

Alternative modifications of the capsid structure which substitute specific sequences from other genotypes of HCV may be accomplished by the similar use of other synthetic oligonucleotide pairs with StyI/StyI cohesive ends. For example, an amino acid sequence corresponding to the HCV capsid of genotype 2 may be substituted by annealing a synthetic oligonucleotide pair with the sequences given by nucleotides 213 to 259 and the complement of nucleotides 217 to 263 of SEQ ID NO:11 and inserting the duplex into the StyI/StyI region. The capsid encoded by the resulting pGEX-C I2OH-IS02 is given in SEQ ID NO:12. Plasmid pGEX-C 12OH-ISO3 encoding particular amino acids corresponding to an HCV capsid protein of genotype 3 (SEQ ID NO:14 is similarly obtained with the synthetic sequences given by nucleotides 213 to 259 and the complement of nucleotides 217 to 263 of SEQ ID NO:13.

Example 5

Preparation of Purified HCV 1–120 Capsid Proteins

A. Transformation and Growth of Bacteria

Competent *E. coli* (strain W3110, 100 ul bacterial suspension) were transformed with 1 ul of purified pGEX-C120H-V68 plasmid containing the insert shown in SEQ ID NO:7. After 60 minutes on ice, the bacteria were diluted to I ml with LB medium and incubated for a further 60 minutes at 30° C. Aliquots of the culture were than plated on Amp-containing agar plates which were incubated at 30° C. for at least 24 hours. A colony was picked and inoculated into 5 ml of LB medium. After approximately 6 hours at 30° C., 1 ml of the growing culture, indicated by developing turbidity of the inoculum, was then transferred to a 1 liter flask for further overnight sub-culturing, using a temperature controlled shaker at 300 rpm. The main culture was initiated the following morning by inoculating each of 6 flasks containing 0.9 liter of LB and 50 mg ampicillin/liter with 100 ml of the overnight culture. The flasks were shaken at 350 rpm for 2 hours and the cultures were then induced by raising the temperature to 42° C. for 4 hours. The cells were harvested by centrifugation and typically stored frozen until used for purification.

B. Isolation of HCV Capsid Protein from Induced Cultures

The cell paste from 6 liter cultures (approximately 30 g of frozen bacteria) was thawed and suspended in an equal volume of 0.2 M phosphate buffer, pH 7.0, containing 10 mM EDTA and 10 mM benzamidine. Lysozyme (1 mg/g cell paste) and PMSF (0.2 mg/g cell paste) were added and the suspension stirred for approximately 30 minutes at room temperature. During this period, the material became very viscous. The cells were then placed in an ice bath and subjected to 3 minutes of sonication on ice with intervening cooling periods of 1–2 minutes. Soluble materials were removed by centrifugation (Sorvall, SS-34 rotor, 20,000 rpm for 30 minutes) and the extraction procedure was repeated using 0.2 M phosphate buffer containing 10 mM EDTA and 10 mM benzamidine. The combined supernatants were discarded and the sediment suspended in 0.02 M Tris-HCl buffer, pH 8.6, containing 6 M urea. The suspension was subjected to a further cycle of sonication on ice (60 seconds) and the centrifugation was repeated. The supernatant was saved and the sediment re-extracted once, using urea-tris buffer of the same composition. The combined supernatants were treated with ammonium sulfate (0.3 g/ml of solution), kept at 4° C. for about 30 minutes and then centrifuged as described above. A large precipitate had formed which was dissolved in approximately 20 ml of 0.1 M phosphate buffer, pH 7.0, containing 5 mM EDTA and 6 M guanidine-HCl. The solubilized material was clarified by renewed centrifugation and then applied to a 5×105 cm column, containing Sepharose S-300 gel and equilibrated with the same buffer. Fractions (10 ml) were eluted and, following dialysis against 6 M urea of selected aliquots, analyzed by SDS gel electrophoresis. Based on the gel pattern, appropriate fractions were pooled and exhaustively dialyzed against 4 M urea containing 0.1 M sodium acetate buffer, pH 5.4. The dialyzed, clear solution was applied to a column (2.5×20 cm) of CM-Sepharose equilibrated with 4 M urea-0.1 M acetate buffer, pH 5.4. Following application of the sample and washing to remove non-bound constituents, the protein of interest was eluted with a salt gradient (250×250 ml, 0–0.4 M NaCl in the initial urea-containing acetate buffer) and monitored by analysis of selected fractions by 16% SDS PAGE. Fractions containing pure protein were pooled and stored at frozen at −20° C. FIG. 3 shows an analytical SDS gel of purified capsid protein after being subjected to the procedure described.

Example 6

Formation of a Fusion Protein Comprising GST and Amino Acids 21–40 of the HCV Capsid Protein A. Construction of Plasmids Encoding GST-Capsid Fusion Proteins (1) Construction of a Hybrid Gene in pGEX-2T-CAP-B Oligonucleotides 21–40(+) and 21–40(−) for constructing the vector pGEX-2T-CAP-B for expressing the CAP-B fusion protein were prepared as described in Example 4.A.(2) having nucleotide base sequences corresponding to SEQ ID NO:24 and SEQ ID NO:25, respectively.

Oligonucleotides 21–40 (+) and 21–40 (−) were admixed in equal amounts with the pGEX-2T expression vector (Pharmacia) that had been predigested with EcoRI and BamHI and maintained under annealing conditions to allow hybridization of the complementary oligonucleotides and to allow the cohesive termini of the resulting double-stranded oligonucleotide product to hybridize with pGEX-2T at the EcoRI and BamHI cohesive termini. After ligation the resulting plasmid, designated pGEX-2T-CAP-B contains a single copy of the double-stranded oligonucleotide product and contains a structural gene coding for a fusion protein designated CAP-B, having an amino acid residue sequence shown in SEQ ID NO:18 from residue 1 to residue 252.

(2) Insertion of Hybrid Gene into pGEX7-CAP-B1 for High Level Expression

A PCR reaction is performed using the primer pair with sequences given by SEQ ID NO:26 and SEQ ID NO:27 to amplify a 759 base pair fragment from plasmid pGEX-2T-CAP-B. The amplified fragment will contain a single NdeI and EcoRI site at the 5' and 3' ends, respectively.

The PCR product is cut with the NdeI and EcoRI. In a second digestion, the pGEX7 vector is separately digested with NdeI and EcoRI. Following isolation by preparative electrophoresis in 5% acrylamide of each DNA segment, a ligation mixture containing the isolated and restricted PCR reaction product and pGEX7 vector is formed, and incubated with T4 Ligase overnight at 16° C. The mixture is then transformed into competent cells. Colonies are selected for plasmid mini-preparations which can subsequently be analyzed by redigestion with NdeI and EcoRI. The resulting sequence is shown in SEQ ID NO: 17.

B. Structure of the Expressed CAP-B1 Protein

The fusion protein expressed by pGEX7-CAP-B is comprised of an amino-terminal polypeptide portion corresponding to residues 1–220 of glutathione-S-transferase, an intermediate polypeptide portion corresponding to residues 221–226 and defining a cleavage site for Thrombin, and a polypeptide portion corresponding to residues 227–246 defining a portion of the HCV capsid antigen that has the amino acid residue sequence 21–40 in SEQ ID NO:10. CAP-B1 is identical to CAP-B except that it lacks the 6 amino acid residue tail following the residues that correspond to amino acids 21–40 of the HCV capsid.

Example 7

Formation of Recombinant Carrier Free HCV Non-structural Antigen 794

A. Construction of Plasmid Comprising Gene for 794 Antigen Joined to pGEX7

The gene for the nonstructural 794 antigen was prepared from clone 20 (Table 9 p. 109), the latter disclosed in PCT application PCT/US91/06037 and encompassing 105 amino acid codons of the NS3 region inserted into the SmaI site of the vector pUC18. The pUC18 vector containing the insert was redigested with SmaI and EcoRI and subsequently inserted into a similarly digested pGST-2T vector (GenBank Accession number XXU13850). This resulted in an expression vector producing a fusion protein with a contiguous GST-HCV NS3 fusion sequence, GST translation beginning at nucleotide 258 of the vector, the NS3 protein beginning at nucleotide 936. The NS3 gene was re-isolated from this vector by digesting with SmaI and EcoRI, which released a 330 base-pair fragment isolated by preparative electrophoresis.

The pGEX7 vector was modified as follows. A pair of complementary synthetic oligonucleotides with sequences given by SEQ ID NO:28 and SEQ ID NO:29, when annealed, form a duplex with protruding NdeI and BamHI cohesive ends. The duplex encodes 6 histidine residues as well as a SmaI and EcoRI restriction site, the latter followed by stop codons in all three reading frames. To insert the DNA segment into pGEX7, the vector was first digested with NdeI and BamHI and the intervening polylinker removed by electrophoresis. Ligation of the digested vector with the synthetic oligonucleotide was followed by transformation and analysis of several mini-preparations. The plasmids were screened for a SmaI restriction site which is present in the insert but not the parent vector. Of ten colonies screened, all showed the presence of the SmaI restriction site. A colony was picked and used for preparing a sufficient quantity of modified pGEX7 plasmid. The plasmid was then linearized by digesting with SmaI and EcoRI the vector fragment was separated from the small SmaI-EcoRI fragment. The digested modified pGEX7 vector was used for ligation with the gene for the nonstructural NS3 antigen.

Ligation of the digested modified pGEX7 vector and the SmaI-EcoRI fragment encompassing the gene for the NS3 antigen was carried out overnight in the presence of 400 U of T4 DNA ligase and 1 mM ATP. Transformation of the ligase mixture was followed by screening of mini-preparations which identified several clones that contained the inserted gene for the 794 antigen as indicated by electrophoresis in a 5% acrylamide gel. Several of these clones also expressed a protein of the expected molecular size in mini-inductions. One of the clones was selected for a 6 liter fermentation experiment. The fermentation/induction was carried as described in Example 5A.

B. Purification of 794 Antigen from Fermentation Broths

Frozen cell paste from induced cultures was thawed, suspended in buffer (0.2 M phosphate, 10 mM EDTA, 10 mM Benzamidine) and treated with lysozyme (1 mg/g cell paste) and PMSF (0.2 mg/g cell paste) followed by sonication as described in Example 5B. Following centrifugation, it was discovered that the protein of interest was directly soluble in the aqueous supernatant. Therefore, the sediment was discarded and the supernatant subjected to gel chromatography on a column (2.5×110 cm) of Sepharose S-300 eluted with 0.02 M Tris-HCl, pH 8.6, containing 0.2 M NaCl. Fractions were monitored with SDS PAGE and those containing the protein of interest pooled. The pooled material was subsequently applied in aliquots to a column (1×5 cm) of iminodiacetic acid derivatized Sepharose which had been previously charged with 50 mM nickel chloride and washed with 0.02 M Tris-HCl, 0.2 M NaCl. After absorption of the hexahistidine derivative of the NS3 794 antigen, it was eluted using successive elution steps with 0.03M Imidazole and 0.3 M Imidazole, respectively, in the above buffer. The protein emerged as a sharp peak with 0.3 M imidazole and was subsequently stored frozen at −20° C. An SDS PAGE analysis of the purified material is shown in FIG. 4.

Example 8

Immune Reactivity of HCV Recombinant Antigens Expressed in pGEX7 Vectors

Polystyrene wells (Nunc, Polysorp) were coated with mixtures of the HCV capsid polypeptide (SEQ ID NO:8) in concentrations ranging between 1 and 4 $\mu$g/ml and the HCV 794 NS3 antigen (SEQ ID NO:16) at 0.2–0.5 $\mu$g/ml. After blocking with 3% bovine serum albumin the plates were dried under vacuum and then used to analyze the immune reactivity against sera from individuals undergoing seroconversion and therefore known to develop antibody against HCV. The results are shown in FIGS. 6–8, each of which provide the signal to cut off values recorded for the assay using the source materials of the present invention and compared with the data from commercial immunoassays as supplied by the manufacturer of the conversion panels. These assays detected antibody at least as early, or earlier than the state-of-the art assays.

We claim:

1. A recombinant DNA molecule comprising a vector having a procaryotic promoter operatively linked to a DNA segment, said DNA segment composed of a first nucleotide base sequence operatively linked in frame at its 3' terminus to the 5' terminus of a second nucleotide base sequence, said first sequence having a nucleotide base sequence represented by the formula:

AGGAGGGTTTTTCAT, corresponding to nucleotides 1–15 of SEQ ID NO.: 1, and said second sequence consists of a nucleotide sequence encoding amino acids 1–120 of the HCV capsid antigen.

2. The vector of claim 1, wherein said vector is pGEX7 comprising said first nucleic and second nucleic acids.

3. The vector of claim 1, wherein said amino acids are amino acids 1–120 of SEQ ID NO:8.

4. The vector of claim 3, wherein said vector is pGEX-C120H-V68.

5. The vector of claim 1, wherein said amino acids are amino acids 1–120 of SEQ ID NO:10.

6. The vector of claim 5, wherein said vector is said vector is pGEX-C120H.

7. The vector of claim 1, wherein said amino acids are amino acids 1–120 of SEQ ID NO:12.

8. The vector of claim 7, wherein said vector is pGEX-C120H-ISO2.

9. The vector of claim 1, wherein said amino acids are amino acids 1–120 of SEQ ID NO:14.

10. The vector of claim 9, wherein said vector is pGEX-C120H-ISO3.

11. A procaryotic host cell comprising an expression vector of any one of claims 1, 3, 5, 7 or 9.

12. A method of producing an HCV capsid antigen consisting of amino acid residues 1–120 which comprises:

(a) treating a host cell comprising an expression vector of any one of claims 1, 3, 5, 7 and 9 under conditions and for a time effective to express said antigen; and (b) recovering said antigen from the fermentation broth following expression by using standard biochemical isolation techniques involving (i) harvest of the bacterial culture (ii) disruption of isolated cell paste (iii) differential extraction and centrifigutation of disrupted cells (iv) gel sizing and cationic exchange chromatography steps to separate the HCV capsid antigen from contaminating materials and (v) collecting the purified HCV antigen for its designated use.

13. A recombinant HCV capsid antigen produced by the method of claim 12.

14. A composition comprising a recombinant HCV capsid antigen of claim 13, wherein said composition is essentially free of procaryotic antigens and other HCV-related prote

UNITED STATES PATENT AND TRADEMARK OFFICE
CERTIFICATE OF CORRECTION

PATENT NO.    : 6,692,751 B1
DATED         : February 17, 2004
INVENTOR(S)   : Suzanne Zebedee et al.

It is certified that error appears in the above-identified patent and that said Letters Patent is hereby corrected as shown below:

<u>Title page,</u>
Item [73], Assignee, please add the following:
-- Suzanne Zebedee assignor to Torsten B. Helting --

Signed and Sealed this

Fourth Day of May, 2004

JON W. DUDAS
*Acting Director of the United States Patent and Trademark Office*

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 795 base pairs
      (B) TYPE: nucleic acid
      (C) STRANDEDNESS: single
      (D) TOPOLOGY: linear (ii) MOLECULE TYPE: Genomic DNA (iii) HYPOTHETICAL: no (iv) ANTI-SENSE: no (ix) FEATURE:
      (A) NAME/KEY: CDS
      (B) LOCATION: 16-789

(xi) SEQUENCE DESCRIPTION: SEQ ID NO:1:

```
AGGAGGGTTT TTCAT ATG CCA ATC GTG CAG AAC ATC CAG GGG CAA ATG GTA        51
                 Met Pro Ile Val Gln Asn Ile Gln Gly Gln Met Val
                  1               5                  10

CAT CAG GCC ATA TCA CCT AGA ACT TTA AAT GCA TGG GTA AAA GTA GTA         99
His Gln Ala Ile Ser Pro Arg Thr Leu Asn Ala Trp Val Lys Val Val
         15                  20                  25

GAA GAG AAG GCT TTC AGC CCA GAA GTG ATA CCC ATG TTT TCA GCA TTA        147
Glu Glu Lys Ala Phe Ser Pro Glu Val Ile Pro Met Phe Ser Ala Leu
 30                  35                  40

TCA GAA GGA GCC ACC CCA CAA GAT TTA AAC ACC ATG CTA AAC ACA GTG        195
Ser Glu Gly Ala Thr Pro Gln Asp Leu Asn Thr Met Leu Asn Thr Val
45                  50                  55                  60

GGG GGA CAT CAA GCA GCC ATG CAA ATG TTA AAA GAG ACC ATC AAT GAG        243
Gly Gly His Gln Ala Ala Met Gln Met Leu Lys Glu Thr Ile Asn Glu
                 65                  70                  75

GAA GCT GCA GAA TGG GAT AGA GTG CAT CCA GTG CAT GCA GGG CCT ATT        291
Glu Ala Ala Glu Trp Asp Arg Val His Pro Val His Ala Gly Pro Ile
 80                  85                  90

GCA CCA GGC CAG ATG AGA GAA CCA AGG GGA AGT GAC ATA GCA GGA ACT        339
Ala Pro Gly Gln Met Arg Glu Pro Arg Gly Ser Asp Ile Ala Gly Thr
         95                  100                 105

ACT AGT ACC CTT CAG GAA CAA ATA GGA TGG ATG ACA AAT AAT CCA CCT        387
Thr Ser Thr Leu Gln Glu Gln Ile Gly Trp Met Thr Asn Asn Pro Pro
    110                 115                 120

ATC CCA GTA GGA GAA ATT TAT AAA AGA TGG ATA ATC CTG GGA TTA AAT        435
Ile Pro Val Gly Glu Ile Tyr Lys Arg Trp Ile Ile Leu Gly Leu Asn
125                 130                 135                 140

AAA ATA GTA AGA ATG TAT AGC CCT ACC AGC ATT CTG GAC ATA AGA CAA        483
Lys Ile Val Arg Met Tyr Ser Pro Thr Ser Ile Leu Asp Ile Arg Gln
                145                 150                 155

GGA CCA AAG GAA CCC TTT AGA GAC TAT GTA GAC CGG TTC TAT AAA ACT        531
Gly Pro Lys Glu Pro Phe Arg Asp Tyr Val Asp Arg Phe Tyr Lys Thr
        160                 165                 170

CTA AGA GCC GAG CAA GCT TCA CAG GAG GTA AAA AAT TGG ATG ACA GAA        579
Leu Arg Ala Glu Gln Ala Ser Gln Glu Val Lys Asn Trp Met Thr Glu
    175                 180                 185

ACC TTG TTG GTC CAA AAT GCG AAC CCA GAT TGT AAG ACT ATT TTA AAA        627
Thr Leu Leu Val Gln Asn Ala Asn Pro Asp Cys Lys Thr Ile Leu Lys
    190                 195                 200
```

```
GCA TTG GGA CCA GCG GCT ACA CTA GAA GAA ATG ATG ACA GCA TGT CAG        675
Ala Leu Gly Pro Ala Ala Thr Leu Glu Glu Met Met Thr Ala Cys Gln
205             210                 215                 220

GGA GTA GGA GGA CCC AAA AAT CAA CAA TTA TTA TCC TTA TGG GGG TGT        723
Gly Val Gly Gly Pro Lys Asn Gln Gln Leu Leu Ser Leu Trp Gly Cys
                225                 230                 235

AAA GGG AAA CTT GTT TGT TAT ACT TCC GTT AAA TGG AAT GGA CCC GGC        771
Lys Gly Lys Leu Val Cys Tyr Thr Ser Val Lys Trp Asn Gly Pro Gly
                240                 245                 250

CAT AAG GCA AGA GTT TTG TAA TAA                                        795
His Lys Ala Arg Val Leu
        255
```

(2) INFORMATION FOR SEQ ID NO:2:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Ile Val Gln Asn Ile Gln Gly Gln Met Val His Gln Ala Ile
                5                   10                  15

Ser Pro Arg Thr Leu Asn Ala Trp Val Lys Val Val Glu Glu Lys Ala
                20                  25                  30

Phe Ser Pro Glu Val Ile Pro Met Phe Ser Ala Leu Ser Glu Gly Ala
            35                  40                  45

Thr Pro Gln Asp Leu Asn Thr Met Leu Asn Thr Val Gly Gly His Gln
50                  55                  60

Ala Ala Met Gln Met Leu Lys Glu Thr Ile Asn Glu Glu Ala Ala Glu
65                  70                  75                  80

Trp Asp Arg Val His Pro Val His Ala Gly Pro Ile Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr Asn Asn Pro Pro Ile Pro Val Gly
            115                 120                 125

Glu Ile Tyr Lys Arg Trp Ile Ile Leu Gly Leu Asn Lys Ile Val Arg
130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Glu Val Lys Asn Trp Met Thr Glu Thr Leu Leu Val
            180                 185                 190

Gln Asn Ala Asn Pro Asp Cys Lys Thr Ile Leu Lys Ala Leu Gly Pro
            195                 200                 205

Ala Ala Thr Leu Glu Glu Met Met Thr Ala Cys Gln Gly Val Gly Gly
            210                 215                 220

Pro Lys Asn Gln Gln Leu Leu Ser Leu Trp Gly Cys Lys Gly Lys Leu
225                 230                 235                 240

Val Cys Tyr Thr Ser Val Lys Trp Asn Gly Pro Gly His Lys Ala Arg
                245                 250                 255

Val Leu
```

(2) INFORMATION FOR SEQ ID NO:3:

(i) SEQUENCE CHARACTERISTICS:
        (A) LENGTH: 795 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (ix) FEATURE:
        (A) NAME/KEY: CDS
        (B) LOCATION: 16-789

(xi) SEQUENCE DESCRIPTION: SEQ ID NO:3:

```
AGGAGGGTTT TTCAT ATG CCA ATC GTG CAG AAC ATC CAG GGG CAA ATG GTA        51
                 Met Pro Ile Val Gln Asn Ile Gln Gly Gln Met Val
                   1               5                  10

CAT CAG GCC ATA TCA CCT AGA ACT TTA AAT GCA TGG GTA AAA GTA GTA         99
His Gln Ala Ile Ser Pro Arg Thr Leu Asn Ala Trp Val Lys Val Val
         15                  20                  25

GAA GAG AAG GCT TTC AGC CCA GAA GTG ATA CCC ATG TTT TCA GCA TTA        147
Glu Glu Lys Ala Phe Ser Pro Glu Val Ile Pro Met Phe Ser Ala Leu
     30                  35                  40

TCA GAA GGA GCC ACC CCA CAA GAT TTA AAC ACC ATG CTA AAC ACA GTG        195
Ser Glu Gly Ala Thr Pro Gln Asp Leu Asn Thr Met Leu Asn Thr Val
 45                  50                  55                  60

GGG GGA CAT CAA GCA GCC ATG CAA ATG TTA AAA GAG ACC ATC AAT GAG        243
Gly Gly His Gln Ala Ala Met Gln Met Leu Lys Glu Thr Ile Asn Glu
             65                  70                  75

GAA GCT GCA GAA TGG GAT AGA GTG CAT CCA GTG CAT GCA GGG CCT ATT        291
Glu Ala Ala Glu Trp Asp Arg Val His Pro Val His Ala Gly Pro Ile
         80                  85                  90

GCA CCA GGC CAG ATG AGA GAA CCA AGG GGA AGT GAC ATA GCA GGA ACT        339
Ala Pro Gly Gln Met Arg Glu Pro Arg Gly Ser Asp Ile Ala Gly Thr
     95                 100                 105

ACT AGT ACC CTT CAG GAA CAA ATA GGA TGG ATG ACA AAT AAT CCA CCT        387
Thr Ser Thr Leu Gln Glu Gln Ile Gly Trp Met Thr Asn Asn Pro Pro
110                 115                 120

ATC CCA GTA GGA GAA ATT TAT AAA AGA TGG ATA ATC CTG GGA TTA AAT        435
Ile Pro Val Gly Glu Ile Tyr Lys Arg Trp Ile Ile Leu Gly Leu Asn
125                 130                 135                 140

AAA ATA GTA AGA ATG TAT AGC CCT ACC AGC ATT CTG GAC ATA AGA CAA        483
Lys Ile Val Arg Met Tyr Ser Pro Thr Ser Ile Leu Asp Ile Arg Gln
                145                 150                 155

GGA CCA AAG GAA CCC TTT AGA GAC TAT GTA GAC CGG TTC TAT AAA ACT        531
Gly Pro Lys Glu Pro Phe Arg Asp Tyr Val Asp Arg Phe Tyr Lys Thr
            160                 165                 170

CTA AGA GCC GAG CAA GCT TCA CAG GAG GTA AAA AAT TGG ATG ACA GAA        579
Leu Arg Ala Glu Gln Ala Ser Gln Glu Val Lys Asn Trp Met Thr Glu
        175                 180                 185

ACC TTG TTG GTC CAA AAT GCG AAC CCA GAT TGT AAG ACT ATT TTA AAA        627
Thr Leu Leu Val Gln Asn Ala Asn Pro Asp Cys Lys Thr Ile Leu Lys
    190                 195                 200

GCA TTG GGA CCA GCG GCT ACA CTA GAA GAA ATG ATG ACA GCA TGT CAG        675
Ala Leu Gly Pro Ala Ala Thr Leu Glu Glu Met Met Thr Ala Cys Gln
205                 210                 215                 220

GGA GTA GGA GGA CCC AAA AAT CAA CAA AGA TTA AAT TTA TGG GGG TGT        723
Gly Val Gly Gly Pro Lys Asn Gln Gln Arg Leu Asn Leu Trp Gly Cys
```

```
                          225                  230                  235
AAA GGG AAA CTT ATT TGT TAT ACT TCC GTT AAA TGG AAT GGA CCC GGC        771
Lys Gly Lys Leu Ile Cys Tyr Thr Ser Val Lys Trp Asn Gly Pro Gly
                240                  245                  250

CAT AAG GCA AGA GTT TTG TAA TAA                                        795
His Lys Ala Arg Val Leu
```

(2) INFORMATION FOR SEQ ID NO:4:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:4:

```
Met Pro Ile Val Gln Asn Ile Gln Gly Gln Met Val His Gln Ala Ile
                5                   10                  15

Ser Pro Arg Thr Leu Asn Ala Trp Val Lys Val Glu Glu Lys Ala
            20                  25                  30

Phe Ser Pro Glu Val Ile Pro Met Phe Ser Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80

Trp Asp Arg Val His Pro Val His Ala Gly Pro Ile Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr Asn Asn Pro Pro Ile Pro Val Gly
        115                 120                 125

Glu Ile Tyr Lys Arg Trp Ile Ile Leu Gly Leu Asn Lys Ile Val Arg
    130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Glu Val Lys Asn Trp Met Thr Glu Thr Leu Leu Val
            180                 185                 190

Gln Asn Ala Asn Pro Asp Cys Lys Thr Ile Leu Lys Ala Leu Gly Pro
        195                 200                 205

Ala Ala Thr Leu Glu Glu Met Met Thr Ala Cys Gln Gly Val Gly Gly
    210                 215                 220

Pro Lys Asn Gln Gln Arg Leu Asn Leu Trp Gly Cys Lys Gly Lys Leu
225                 230                 235                 240

Ile Cys Tyr Thr Ser Val Lys Trp Asn Gly Pro Gly His Lys Ala Arg
                245                 250                 255

Val Leu
```

(2) INFORMATION FOR SEQ ID NO:5:

(i) SEQUENCE CHARACTERISTICS:
        (A) LENGTH: 795 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (ix) FEATURE:
    (A) NAME/KEY: CDS
    (B) LOCATION: 16-789

(xi) SEQUENCE DESCRIPTION: SEQ ID NO:5:

```
AGGAGGGTTT TTCAT ATG CCA ATC GTG CAG AAC ATC CAG GGG CAA ATG GTA        51
                 Met Pro Ile Val Gln Asn Ile Gln Gly Gln Met Val
                   5                  10

CAT CAG GCC ATA TCA CCT AGA ACT TTA AAT GCA TGG GTA AAA GTA GTA        99
His Gln Ala Ile Ser Pro Arg Thr Leu Asn Ala Trp Val Lys Val Val
         15                  20                  25

GAA GAG AAG GCT TTC AGC CCA GAA GTG ATA CCC ATG TTT TCA GCA TTA        147
Glu Glu Lys Ala Phe Ser Pro Glu Val Ile Pro Met Phe Ser Ala Leu
     30                  35                  40

TCA GAA GGA GCC ACC CCA CAA GAT TTA AAC ACC ATG CTA AAC ACA GTG        195
Ser Glu Gly Ala Thr Pro Gln Asp Leu Asn Thr Met Leu Asn Thr Val
45                  50                  55                  60

GGG GGA CAT CAA GCA GCC ATG CAA ATG TTA AAA GAG ACC ATC AAT GAG        243
Gly Gly His Gln Ala Ala Met Gln Met Leu Lys Glu Thr Ile Asn Glu
             65                  70                  75

GAA GCT GCA GAA TGG GAT AGA GTG CAT CCA GTG CAT GCA GGG CCT ATT        291
Glu Ala Ala Glu Trp Asp Arg Val His Pro Val His Ala Gly Pro Ile
                 80                  85                  90

GCA CCA GGC CAG ATG AGA GAA CCA AGG GGA AGT GAC ATA GCA GGA ACT        339
Ala Pro Gly Gln Met Arg Glu Pro Arg Gly Ser Asp Ile Ala Gly Thr
         95                 100                 105

ACT AGT ACC CTT CAG GAA CAA ATA GGA TGG ATG ACA AAT AAT CCA CCT        387
Thr Ser Thr Leu Gln Glu Gln Ile Gly Trp Met Thr Asn Asn Pro Pro
     110                 115                 120

ATC CCA GTA GGA GAA ATT TAT AAA AGA TGG ATA ATC CTG GGA TTA AAT        435
Ile Pro Val Gly Glu Ile Tyr Lys Arg Trp Ile Ile Leu Gly Leu Asn
125                 130                 135                 140

AAA ATA GTA AGA ATG TAT AGC CCT ACC AGC ATT CTG GAC ATA AGA CAA        483
Lys Ile Val Arg Met Tyr Ser Pro Thr Ser Ile Leu Asp Ile Arg Gln
             145                 150                 155

GGA CCA AAG GAA CCC TTT AGA GAC TAT GTA GAC CGG TTC TAT AAA ACT        531
Gly Pro Lys Glu Pro Phe Arg Asp Tyr Val Asp Arg Phe Tyr Lys Thr
                 160                 165                 170

CTA AGA GCC GAG CAA GCT TCA CAG GAG GTA AAA AAT TGG ATG ACA GAA        579
Leu Arg Ala Glu Gln Ala Ser Gln Glu Val Lys Asn Trp Met Thr Glu
         175                 180                 185

ACC TTG TTG GTC CAA AAT GCG AAC CCA GAT TGT AAG ACT ATT TTA AAA        627
Thr Leu Leu Val Gln Asn Ala Asn Pro Asp Cys Lys Thr Ile Leu Lys
     190                 195                 200

GCA TTG GGA CCA GCG GCT ACA CTA GAA GAA ATG ATG ACA GCA TGT CAG        675
Ala Leu Gly Pro Ala Ala Thr Leu Glu Glu Met Met Thr Ala Cys Gln
205                 210                 215                 220

GGA GTA GGA GGA CCA CAA AAT CAA CAA CTT TTA AAT TTA TGG GGG TGT        723
Gly Val Gly Gly Pro Gln Asn Gln Gln Leu Leu Asn Leu Trp Gly Cys
             225                 230                 235

AGA GGG AAA GCT ATT TGT TAT ACT TCC GTT CAA TGG AAT GGA CCC GGC        771
Arg Gly Lys Ala Ile Cys Tyr Thr Ser Val Gln Trp Asn Gly Pro Gly
                 240                 245                 250

CAT AAG GCA AGA GTT TTG TAA TAA                                        795
His Lys Ala Arg Val Leu
```

(2) INFORMATION FOR SEQ ID NO:6:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:6:

```
Met Pro Ile Val Gln Asn Ile Gln Gly Gln Met Val His Gln Ala Ile
                 5                  10                  15
Ser Pro Arg Thr Leu Asn Ala Trp Val Lys Val Glu Glu Lys Ala
             20                  25                  30
Phe Ser Pro Glu Val Ile Pro Met Phe Ser Ala Leu Ser Glu Gly Ala
             35                  40                  45
Thr Pro Gln Asp Leu Asn Thr Met Leu Asn Thr Val Gly Gly His Gln
         50                  55                  60
Ala Ala Met Gln Met Leu Lys Glu Thr Ile Asn Glu Glu Ala Ala Glu
 65                  70                  75                  80
Trp Asp Arg Val His Pro Val His Ala Gly Pro Ile Ala Pro Gly Gln
                 85                  90                  95
Met Arg Glu Pro Arg Gly Ser Asp Ile Ala Gly Thr Thr Ser Thr Leu
                100                 105                 110
Gln Glu Gln Ile Gly Trp Met Thr Asn Asn Pro Pro Ile Pro Val Gly
            115                 120                 125
Glu Ile Tyr Lys Arg Trp Ile Ile Leu Gly Leu Asn Lys Ile Val Arg
        130                 135                 140
Met Tyr Ser Pro Thr Ser Ile Leu Asp Ile Arg Gln Gly Pro Lys Glu
145                 150                 155                 160
Pro Phe Arg Asp Tyr Val Asp Arg Phe Tyr Lys Thr Leu Arg Ala Glu
                165                 170                 175
Gln Ala Ser Gln Glu Val Lys Asn Trp Met Thr Glu Thr Leu Leu Val
            180                 185                 190
Gln Asn Ala Asn Pro Asp Cys Lys Thr Ile Leu Lys Ala Leu Gly Pro
        195                 200                 205
Ala Ala Thr Leu Glu Glu Met Met Thr Ala Cys Gln Gly Val Gly Gly
    210                 215                 220
Pro Gln Asn Gln Gln Leu Leu Asn Leu Trp Gly Cys Arg Gly Lys Ala
225                 230                 235                 240
Ile Cys Tyr Thr Ser Val Gln Trp Asn Gly Pro Gly His Lys Ala Arg
                245                 250                 255
Val Leu
```

(2) INFORMATION FOR SEQ ID NO:7:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (ix) FEATURE:
    (A) NAME/KEY: CDS
    (B) LOCATION: 16-375

(xi) SEQUENCE DESCRIPTION: SEQ ID NO:7:

```
AGGAGGGTTT TTCAT ATG AGC ACG AAT CCT AAA CCT CAA AGA AAA ACC AAA        51
              Met Ser Thr Asn Pro Lys Pro Gln Arg Lys Thr Lys
                   5                   10

CGT AAC ACC AAC CGT CGC CCA CAG GAC GTC AAG TTC CCG GGT GGC GGT         99
Arg Asn Thr Asn Arg Arg Pro Gln Asp Val Lys Phe Pro Gly Gly Gly
         15                  20                  25

CAG ATC GTT GGT GGA GTT TAC TTG TTG CCG CGC AGG GGC CCT AGA TTG        147
Gln Ile Val Gly Gly Val Tyr Leu Leu Pro Arg Arg Gly Pro Arg Leu
     30                  35                  40

GGT GTG CGC GCG ACG AGG AAG ACT TCC GAG CGG TCG CAA CCT CGA GGT        195
Gly Val Arg Ala Thr Arg Lys Thr Ser Glu Arg Ser Gln Pro Arg Gly
 45                  50                  55                  60

AGA CGT CAG CCT ATC CCC AAG GTG CGT CGG CCG GAG GGC AGG ACC TGG        243
Arg Arg Gln Pro Ile Pro Lys Val Arg Arg Pro Glu Gly Arg Thr Trp
                 65                  70                  75

GCT CAG CCC GGG TAC CCT TGG CCC CTC TAT GGC AAT GAG GGT TGC GGG        291
Ala Gln Pro Gly Tyr Pro Trp Pro Leu Tyr Gly Asn Glu Gly Cys Gly
             80                  85                  90

TGG GCG GGA TGG CTC CTG TCT CCC CGT GGC TCT CGG CCT AGC TGG GGC        339
Trp Ala Gly Trp Leu Leu Ser Pro Arg Gly Ser Arg Pro Ser Trp Gly
         95                 100                 105

CCC ACA GAC CCC CGG CGT AGG TCG CGC AAT TTG GGT TAA                    378
Pro Thr Asp Pro Arg Arg Arg Ser Arg Asn Leu Gly
     110                 115                 120
```

(2) INFORMATION FOR SEQ ID NO:8:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser Thr Asn Pro Lys Pro Gln Arg Lys Thr Lys Arg Asn Thr Asn
              5                  10                  15

Arg Arg Pro Gln Asp Val Lys Phe Pro Gly Gly Gly Gln Ile Val Gly
         20                  25                  30

Gly Val Tyr Leu Leu Pro Arg Arg Gly Pro Arg Leu Gly Val Arg Ala
     35                  40                  45

Thr Arg Lys Thr Ser Glu Arg Ser Gln Pro Arg Gly Arg Arg Gln Pro
 50                  55                  60

Ile Pro Lys Val Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
             85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly
            115                 120
```

(2) INFORMATION FOR SEQ ID NO:9:

(i) SEQUENCE CHARACTERISTICS:
        (A) LENGTH: 378 base pairs (B) TYPE: nucleic acid
          (C) STRANDEDNESS: single
          (D) TOPOLOGY: linear (ii) MOLECULE TYPE: Genomic DNA (iii) HYPOTHETICAL: no (iv) ANTI-SENSE: no (ix) FEATURE:
          (A) NAME/KEY: CDS
          (B) LOCATION: 16-375

(xi) SEQUENCE DESCRIPTION: SEQ ID NO:9:

```
AGGAGGGTTT TTCAT ATG AGC ACG AAT CCT AAA CCT CAA AGA AAA ACC AAA          51
                 Met Ser Thr Asn Pro Lys Pro Gln Arg Lys Thr Lys
                                  5                  10

CGT AAC ACC AAC CGT CGC CCA CAG GAC GTC AAG TTC CCG GGT GGC GGT           99
Arg Asn Thr Asn Arg Arg Pro Gln Asp Val Lys Phe Pro Gly Gly Gly
             15                  20                  25

CAG ATC GTT GGT GGA GTT TAC TTG TTG CCG CGC AGG GGC CCT AGA TTG          147
Gln Ile Val Gly Gly Val Tyr Leu Leu Pro Arg Arg Gly Pro Arg Leu
         30                  35                  40

GGT GTG CGC GCG ACG AGG AAG ACT TCC GAG CGG TCG CAA CCT CGA GGT          195
Gly Val Arg Ala Thr Arg Lys Thr Ser Glu Arg Ser Gln Pro Arg Gly
 45                  50                  55                  60

AGA CGT CAG CCT ATC CCC AAG GCA CGT CGG CCC GAG GGC AGG ACC TGG          243
Arg Arg Gln Pro Ile Pro Lys Ala Arg Arg Pro Glu Gly Arg Thr Trp
                 65                  70                  75

GCT CAG CCC GGG TAC CCT TGG CCC CTC TAT GGC AAT GAG GGT TGC GGG          291
Ala Gln Pro Gly Tyr Pro Trp Pro Leu Tyr Gly Asn Glu Gly Cys Gly
             80                  85                  90

TGG GCG GGA TGG CTC CTG TCT CCC CGT GGC TCT CGG CCT AGC TGG GGC          339
Trp Ala Gly Trp Leu Leu Ser Pro Arg Gly Ser Arg Pro Ser Trp Gly
         95                  100                 105

CCC ACA GAC CCC CGG CGT AGG TCG CGC AAT TTG GGT TAA                      378
Pro Thr Asp Pro Arg Arg Arg Ser Arg Asn Leu Gly
110                 115                 120
```

(2) INFORMATION FOR SEQ ID NO:10:

(i) SEQUENCE CHARACTERISTICS:
          (A) LENGTH: 120 amino acids
          (B) TYPE: amino acid
          (D) TOPOLOGY: linear (ii) MOLECULE TYPE: protein (xi) SEQUENCE DESCRIPTION: SEQ ID NO:10:

```
Met Ser Thr Asn Pro Lys Pro Gln Arg Lys Thr Lys Arg Asn Thr Asn
                 5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
```

(2) INFORMATION FOR SEQ ID NO:11:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (ix) FEATURE:
        (A) NAME/KEY: CDS
        (B) LOCATION: 16-375

(xi) SEQUENCE DESCRIPTION: SEQ ID NO:11:

```
AGGAGGGTTT TTCAT ATG AGC ACG AAT CCT AAA CCT CAA AGA AAA ACC AAA        51
                 Met Ser Thr Asn Pro Lys Pro Gln Arg Lys Thr Lys
                                  5                      10

CGT AAC ACC AAC CGT CGC CCA CAG GAC GTC AAG TTC CCG GGT GGC GGT         99
Arg Asn Thr Asn Arg Arg Pro Gln Asp Val Lys Phe Pro Gly Gly Gly
         15                  20                  25

CAG ATC GTT GGT GGA GTT TAC TTG TTG CCG CGC AGG GGC CCT AGA TTG        147
Gln Ile Val Gly Gly Val Tyr Leu Leu Pro Arg Arg Gly Pro Arg Leu
     30                  35                  40

GGT GTG CGC GCG ACG AGG AAG ACT TCC GAG CGG TCG CAA CCT CGA GGT        195
Gly Val Arg Ala Thr Arg Lys Thr Ser Glu Arg Ser Gln Pro Arg Gly
45                  50                  55                  60

AGA CGT CAG CCT ATC CCC AAG GAC CGT CGG TCC ACG GGC AAG TCC TGG        243
Arg Arg Gln Pro Ile Pro Lys Asp Arg Arg Ser Thr Gly Lys Ser Trp
                 65                  70                  75

GGT AAG CCC GGG TAC CCT TGG CCC CTC TAT GGC AAT GAG GGT TGC GGG        291
Gly Lys Pro Gly Tyr Pro Trp Pro Leu Tyr Gly Asn Glu Gly Cys Gly
             80                  85                  90

TGG GCG GGA TGG CTC CTG TCT CCC CGT GGC TCT CGG CCT AGC TGG GGC        339
Trp Ala Gly Trp Leu Leu Ser Pro Arg Gly Ser Arg Pro Ser Trp Gly
         95                 100                 105

CCC ACA GAC CCC CGG CGT AGG TCG CGC AAT TTG GGT TAA                    378
Pro Thr Asp Pro Arg Arg Arg Ser Arg Asn Leu Gly
     110                 115                 120
```

(2) INFORMATION FOR SEQ ID NO:12:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ser Thr Asn Pro Lys Pro Gln Arg Lys Thr Lys Arg Asn Thr Asn
                 5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45
```

```
Thr Arg Lys Thr Ser Glu Arg Ser Gln Pro Arg Gly Arg Arg Gln Pro
     50                  55                  60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Thr Asp Pro
                100                 105                 110

Arg Arg Arg Ser Arg Asn Leu Gly
            115                 120
```

(2) INFORMATION FOR SEQ ID NO:13:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (ix) FEATURE:
        (A) NAME/KEY: CDS
        (B) LOCATION: 16-375

(xi) SEQUENCE DESCRIPTION: SEQ ID NO:13:

```
AGGAGGGTTT TTCAT ATG AGC ACG AAT CCT AAA CCT CAA AGA AAA ACC AAA         51
               Met Ser Thr Asn Pro Lys Pro Gln Arg Lys Thr Lys
                                 5                  10

CGT AAC ACC AAC CGT CGC CCA CAG GAC GTC AAG TTC CCG GGT GGC GGT          99
Arg Asn Thr Asn Arg Arg Pro Gln Asp Val Lys Phe Pro Gly Gly Gly
        15                  20                  25

CAG ATC GTT GGT GGA GTT TAC TTG TTG CCG CGC AGG GGC CCT AGA TTG         147
Gln Ile Val Gly Gly Val Tyr Leu Leu Pro Arg Arg Gly Pro Arg Leu
    30                  35                  40

GGT GTG CGC GCG ACG AGG AAG ACT TCC GAG CGG TCG CAA CCT CGA GGT         195
Gly Val Arg Ala Thr Arg Lys Thr Ser Glu Arg Ser Gln Pro Arg Gly
 45                  50                  55                  60

AGA CGT CAG CCT ATC CCC AAG GCA CGT CGG TCC GAG GGC AGG TCC TGG         243
Arg Arg Gln Pro Ile Pro Lys Ala Arg Arg Ser Glu Gly Arg Ser Trp
                 65                  70                  75

GCT CAG CCC GGG TAC CCT TGG CCC CTC TAT GGC AAT GAG GGT TGC GGG         291
Ala Gln Pro Gly Tyr Pro Trp Pro Leu Tyr Gly Asn Glu Gly Cys Gly
             80                  85                  90

TGG GCG GGA TGG CTC CTG TCT CCC CGT GGC TCT CGG CCT AGC TGG GGC         339
Trp Ala Gly Trp Leu Leu Ser Pro Arg Gly Ser Arg Pro Ser Trp Gly
         95                 100                 105

CCC ACA GAC CCC CGG CGT AGG TCG CGC AAT TTG GGT TAA                     378
Pro Thr Asp Pro Arg Arg Arg Ser Arg Asn Leu Gly
        110                 115                 120
```

(2) INFORMATION FOR SEQ ID NO:14:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ser Thr Asn Pro Lys Pro Gln Arg Lys Thr Lys Arg Asn Thr Asn
              5                  10                  15
Arg Arg Pro Gln Asp Val Lys Phe Pro Gly Gly Gly Gln Ile Val Gly
            20                  25                  30
Gly Val Tyr Leu Leu Pro Arg Arg Gly Pro Arg Leu Gly Val Arg Ala
        35                  40                  45
Thr Arg Lys Thr Ser Glu Arg Ser Gln Pro Arg Gly Arg Arg Gln Pro
 50                  55                  60
Ile Pro Lys Ala Arg Arg Ser Glu Gly Arg Ser Trp Ala Gln Pro Gly
 65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly
                115                 120
```

(2) INFORMATION FOR SEQ ID NO:15:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (ix) FEATURE:
        (A) NAME/KEY: CDS
        (B) LOCATION: 16-375

(xi) SEQUENCE DESCRIPTION: SEQ ID NO:15:

```
AGGAGGGTTT TTCAT ATG CCT ATT CAT CAT CAT CAT CAT CAT GGC CCG GGC        51
               Met Pro Ile His His His His His His Gly Pro Gly
                 1               5                      10

TCC GTC ACT GTG TCC CAT CCT AAC ATC GAG GAG GTT GCT CTG TCC ACC         99
Ser Val Thr Val Ser His Pro Asn Ile Glu Glu Val Ala Leu Ser Thr
             15                  20                  25

ACC GGA GAG ATC CCC TTT TAC GGC AAG GCT ATC CCC CTC GAG GTG ATC        147
Thr Gly Glu Ile Pro Phe Tyr Gly Lys Ala Ile Pro Leu Glu Val Ile
 30                  35                  40

AAG GGG GGA AGA CAT CTC ATC TTC TGC CAC TCA AAG AAG AAG TGC GAC        195
Lys Gly Gly Arg His Leu Ile Phe Cys His Ser Lys Lys Lys Cys Asp
 45                  50                  55                  60

GAG CTC GCC GCG AAG CTG GTC GCA TTG GGC ATC AAT GCC GTG GCC TAC        243
Glu Leu Ala Ala Lys Leu Val Ala Leu Gly Ile Asn Ala Val Ala Tyr
                 65                  70                  75

TAC CGC GGT CTT GAC GTG TCT GTC ATC CCG ACC AGC GGC GAT GTT GTC        291
Tyr Arg Gly Leu Asp Val Ser Val Ile Pro Thr Ser Gly Asp Val Val
             80                  85                  90

GTC GTG TCA ACC GAT GCT CTC ATG ACT GGC TTT ACC GGC GAC TTC GAC        339
Val Val Ser Thr Asp Ala Leu Met Thr Gly Phe Thr Gly Asp Phe Asp
         95                  100                 105

TCG GTG ATA GAC TGC AAT ACG GGT ACC GAG CTC GAA TTC TAA                381
Ser Val Ile Asp Cys Asn Thr Gly Thr Glu Leu Glu Phe
    110                 115                 120
```

(2) INFORMATION FOR SEQ ID NO:16:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:16:

```
Met Pro Ile His His His His His Gly Pro Gly Ser Val Thr Val
                 5                  10                  15

Ser His Pro Asn Ile Glu Glu Val Ala Leu Ser Thr Thr Gly Glu Ile
             20                  25                  30

Pro Phe Tyr Gly Lys Ala Ile Pro Leu Glu Val Ile Lys Gly Gly Arg
             35                  40                  45

His Leu Ile Phe Cys His Ser Lys Lys Cys Asp Glu Leu Ala Ala
 50                  55                  60

Lys Leu Val Ala Leu Gly Ile Asn Ala Val Ala Tyr Tyr Arg Gly Leu
 65                  70                  75                  80

Asp Val Ser Val Ile Pro Thr Ser Gly Asp Val Val Val Ser Thr
                 85                  90                  95

Asp Ala Leu Met Thr Gly Phe Thr Gly Asp Phe Asp Ser Val Ile Asp
             100                 105                 110

Cys Asn Thr Gly Thr Glu Leu Glu Phe
             115                 120
```

(2) INFORMATION FOR SEQ ID NO:17:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (ix) FEATURE:
        (A) NAME/KEY: CDS
        (B) LOCATION: 16-771

(xi) SEQUENCE DESCRIPTION: SEQ ID NO:17:

```
AGGAGGGTTT TTCAT ATG TCC CCT ATA CTA GGT TAT TGG AAA ATT AAG GGC      51
                 Met Ser Pro Ile Leu Gly Tyr Trp Lys Ile Lys Gly
                  1               5                  10

CTT GTG CAA CCC ACT CGA CTT CTT TTG GAA TAT CTT GAA GAA AAA TAT       99
Leu Val Gln Pro Thr Arg Leu Leu Leu Glu Tyr Leu Glu Glu Lys Tyr
             15                  20                  25

GAA GAG CAT TTG TAT GAG CGC GAT GAA GGT GAT AAA TGG CGA AAC AAA      147
Glu Glu His Leu Tyr Glu Arg Asp Glu Gly Asp Lys Trp Arg Asn Lys
 30                  35                  40

AAG TTT GAA TTG GGT TTG GAG TTT CCC AAT CTT CCT TAT TAT ATT GAT      195
Lys Phe Glu Leu Gly Leu Glu Phe Pro Asn Leu Pro Tyr Tyr Ile Asp
 45                  50                  55                  60

GGT GAT GTT AAA TTA ACA CAG TCT ATG GCC ATC ATA CGT TAT ATA GCT      243
Gly Asp Val Lys Leu Thr Gln Ser Met Ala Ile Ile Arg Tyr Ile Ala
                 65                  70                  75

GAC AAG CAC AAC ATG TTG GGT GGT TGT CCA AAA GAG CGT GCA GAG ATT      291
Asp Lys His Asn Met Leu Gly Gly Cys Pro Lys Glu Arg Ala Glu Ile
             80                  85                  90
```

-continued

```
TCA ATG CTT GAA GGA GCG GTT TTG GAT ATT AGA TAC GGT GTT TCG AGA       339
Ser Met Leu Glu Gly Ala Val Leu Asp Ile Arg Tyr Gly Val Ser Arg
    95                  100                 105

ATT GCA TAT AGT AAA GAC TTT GAA ACT CTC AAA GTT GAT TTT CTT AGC       387
Ile Ala Tyr Ser Lys Asp Phe Glu Thr Leu Lys Val Asp Phe Leu Ser
    110                 115                 120

AAG CTA CCT GAA ATG CTG AAA ATG TTC GAA GAT CGT TTA TGT CAT AAA       435
Lys Leu Pro Glu Met Leu Lys Met Phe Glu Asp Arg Leu Cys His Lys
125                 130                 135                 140

ACA TAT TTA AAT GGT GAT CAT GTA ACC CAT CCT GAC TTC ATG TTG TAT       483
Thr Tyr Leu Asn Gly Asp His Val Thr His Pro Asp Phe Met Leu Tyr
                145                 150                 155

GAC GCT CTT GAT GTT GTT TTA TAC ATG GAC CCA ATG TGC CTG GAT GCG       531
Asp Ala Leu Asp Val Val Leu Tyr Met Asp Pro Met Cys Leu Asp Ala
            160                 165                 170

TTC CCA AAA TTA GTT TGT TTT AAA AAA CGT ATT GAA GCT ATC CCA CAA       579
Phe Pro Lys Leu Val Cys Phe Lys Lys Arg Ile Glu Ala Ile Pro Gln
        175                 180                 185

ATT GAT AAG TAC TTG AAA TCC AGC AAG TAT ATA GCA TGG CCT TTG CAG       627
Ile Asp Lys Tyr Leu Lys Ser Ser Lys Tyr Ile Ala Trp Pro Leu Gln
    190                 195                 200

GGC TGG CAA GCC ACG TTT GGT GGT GGC GAC CAT CCT CCA AAA TCG GAT       675
Gly Trp Gln Ala Thr Phe Gly Gly Gly Asp His Pro Pro Lys Ser Asp
205                 210                 215                 220

CTG GTT CCG CGT GGA TCC GAC GTC AAG TTC CCG GGT GGC GGT CAG ATC       723
Leu Val Pro Arg Gly Ser Asp Val Lys Phe Pro Gly Gly Gly Gln Ile
                225                 230                 235

GTT GGT GGA GTT TAC TTG TTG CCG CGC AGG GAA TTC ATC GTG ACT GAC       771
Val Gly Gly Val Tyr Leu Leu Pro Arg Arg Glu Phe Ile Val Thr Asp
            240                 245                 250

TGA                                                                    774
```

(2) INFORMATION FOR SEQ ID NO:18:

(i) SEQUENCE CHARACTERISTICS:
        (A) LENGTH: 252 amino acids
        (B) TYPE: amino acid
        (D) TOPOLOGY: linear (ii) MOLECULE TYPE: protein (xi) SEQUENCE DESCRIPTION: SEQ ID NO:18:

```
Met Ser Pro Ile Leu Gly Tyr Trp Lys Ile Lys Gly Leu Val Gln Pro
                5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
            210                 215                 220

Gly Ser Asp Val Lys Phe Pro Gly Gly Gly Gln Ile Val Gly Gly Val
225                 230                 235                 240

Tyr Leu Leu Pro Arg Arg Glu Phe Ile Val Thr Asp
                245                 250

(2) INFORMATION FOR SEQ ID NO:19:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (xi) SEQUENCE DESCRIPTION: SEQ ID NO:19:

CCAAAATTAC CATATGCCAA TCGTGCAGAA C                                    31

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (xi) SEQUENCE DESCRIPTION: SEQ ID NO:20:

GACCCGGCCA TAAGGCAAGA GTTTTGTAAT AAG                                  33

(2) INFORMATION FOR SEQ ID NO:21:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: yes (xi) SEQUENCE DESCRIPTION: SEQ ID NO:21:

```
GATCCTTATT ACAAAACTCT TGCCTTATGG CCGG                                    34

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (xi) SEQUENCE DESCRIPTION: SEQ ID NO:22:

GCTCGCATAT GAGCACGATT CCCAAACC                                           28

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: yes (xi) SEQUENCE DESCRIPTION: SEQ ID NO:23:

GACGAATTCT TAACCCAAAT TGCGCGACCT AC                                      32

(2) INFORMATION FOR SEQ ID NO:24:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (xi) SEQUENCE DESCRIPTION: SEQ ID NO:24:

GATCCGACGT CAAGTTCCCG GGTGGCGGTC AGATCGTTGG TGGAGTTTAC TTGTTGCCGC        60

GCAGGG                                                                   66

(2) INFORMATION FOR SEQ ID NO:25:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: yes (xi) SEQUENCE DESCRIPTION: SEQ ID NO:25:

AATTCCCTGC GCGGCAACAA GTAAACTCCA CCAACGATCT GACCGCCACC CGGGAACTTG        60
```

ACGTCG                                                              66

(2) INFORMATION FOR SEQ ID NO:26:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (xi) SEQUENCE DESCRIPTION: SEQ ID NO:26:

GGAATTCCAT ATGTCCCCTA TACTAGGT                                      28

(2) INFORMATION FOR SEQ ID NO:27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: yes (xi) SEQUENCE DESCRIPTION: SEQ ID NO:27:

CGGAATTCTC ACCTGCGCGG CAACAA                                        26

(2) INFORMATION FOR SEQ ID NO:28:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: no (xi) SEQUENCE DESCRIPTION: SEQ ID NO:28:

TATGCCTATT CATCATCATC ATCATCATGG CCCGGGAATT CTAAGTAAGT AG           52

(2) INFORMATION FOR SEQ ID NO:29:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: no (iv) ANTI-SENSE: yes (xi) SEQUENCE DESCRIPTION: SEQ ID NO:29:

GATCCTACTT ACTTAGAATT CCCGGGCCAT GATGATGATG ATGATGAATA GGCA         54